(12) United States Patent
Anton et al.

(10) Patent No.: US 8,188,057 B2
(45) Date of Patent: *May 29, 2012

(54) MODULATION OF 11BETA-HYDROXYSTERIOD DEHYDROGENASE 1 EXPRESSION FOR THE TREATMENT OF OCULAR DISEASES

(75) Inventors: Ana Isabel Jiménez Anton, Madrid (ES); Ángela Seso Yague, Madrid (ES); María Concepción Jiménez Gomez, Madrid (ES)

(73) Assignee: Sylentis S.A.U., Madrid (ES)

( * ) Notice: Subject to any disclaimer, the term of this patent is extended or adjusted under 35 U.S.C. 154(b) by 773 days.

This patent is subject to a terminal disclaimer.

(21) Appl. No.: 12/091,498

(22) PCT Filed: Oct. 25, 2006

(86) PCT No.: PCT/GB2006/050352
§ 371 (c)(1),
(2), (4) Date: Jun. 10, 2008

(87) PCT Pub. No.: WO2007/049074
PCT Pub. Date: May 3, 2007

(65) Prior Publication Data
US 2011/0160277 A1 Jun. 30, 2011

(30) Foreign Application Priority Data
Oct. 25, 2005 (GB) .................................. 0521716.1

(51) Int. Cl.
*C12N 15/11* (2006.01)
(52) U.S. Cl. ..................................................... 514/44 A
(58) Field of Classification Search .................. 514/44 A
See application file for complete search history.

(56) References Cited

U.S. PATENT DOCUMENTS

| | | | |
|---|---|---|---|
| 4,343,794 A | 8/1982 | Podos et al. | |
| 4,617,299 A | 10/1986 | Knepper | |
| 4,652,586 A | 3/1987 | Nathanson | |
| 4,757,089 A | 7/1988 | Epstein | |
| 4,812,448 A | 3/1989 | Knepper | |
| 5,075,323 A | 12/1991 | Fain et al. | |
| 5,242,943 A | 9/1993 | Louis et al. | |
| 5,260,059 A | 11/1993 | Acott et al. | |
| 5,464,866 A | 11/1995 | Clark et al. | |
| 5,545,626 A | 8/1996 | Stein et al. | |
| 5,585,401 A | 12/1996 | Brandt et al. | |
| 6,365,576 B1 | 4/2002 | Carr | |
| 6,372,249 B1 | 4/2002 | Smith et al. | |
| 6,489,307 B1 | 12/2002 | Phillips et al. | |
| 7,176,304 B2 | 2/2007 | McSwiggen et al. | |
| 7,294,504 B1 | 11/2007 | Wang | |
| 7,462,602 B2 * | 12/2008 | Schultz et al. | 514/44 R |
| 7,521,431 B2 | 4/2009 | Reich et al. | |
| 7,579,457 B2 | 8/2009 | Khvorova et al. | |
| 7,592,324 B2 * | 9/2009 | Shepard et al. | 514/44 R |
| 7,592,325 B2 | 9/2009 | Jimenez et al. | |
| 7,618,814 B2 | 11/2009 | Bentwich | |
| 7,687,665 B2 * | 3/2010 | Yao et al. | 564/162 |
| 7,691,997 B2 | 4/2010 | Khvorova et al. | |
| 7,700,575 B2 * | 4/2010 | Andrew et al. | 514/44 R |
| 8,030,284 B2 * | 10/2011 | Jimenez et al. | 536/24.5 |
| 8,090,542 B2 | 1/2012 | Khvorova et al. | |
| 2002/0055536 A1 | 5/2002 | DeWitte et al. | |
| 2002/0114784 A1 | 8/2002 | Li et al. | |
| 2002/0165158 A1 * | 11/2002 | King | 514/12 |
| 2004/0115641 A1 | 6/2004 | Cowsert et al. | |
| 2004/0167090 A1 | 8/2004 | Monahan et al. | |
| 2004/0198640 A1 | 10/2004 | Leake et al. | |
| 2004/0209832 A1 | 10/2004 | McSwiggen et al. | |
| 2004/0224405 A1 | 11/2004 | Leake et al. | |
| 2004/0235031 A1 | 11/2004 | Schultz et al. | |
| 2004/0259247 A1 | 12/2004 | Tuschl et al. | |
| 2004/0266707 A1 | 12/2004 | Leake et al. | |
| 2005/0020521 A1 | 1/2005 | Rana | |
| 2005/0165049 A1 | 7/2005 | Hulme et al. | |
| 2005/0171039 A1 | 8/2005 | McSwiggen et al. | |
| 2005/0208658 A1 * | 9/2005 | Castonguay | 435/455 |
| 2005/0255487 A1 | 11/2005 | Khvorova et al. | |
| 2006/0058266 A1 | 3/2006 | Manoharan et al. | |
| 2006/0094032 A1 | 5/2006 | Fougerolles et al. | |
| 2006/0172963 A1 | 8/2006 | Shepard et al. | |
| 2006/0172965 A1 | 8/2006 | Shepard et al. | |
| 2006/0257851 A1 | 11/2006 | Bentwich | |
| 2007/0049543 A1 * | 3/2007 | McSwiggen et al. | 514/44 |
| 2007/0093435 A1 | 4/2007 | Andrews et al. | |
| 2007/0167384 A1 | 7/2007 | Leake et al. | |
| 2009/0326044 A1 | 12/2009 | Shepard et al. | |

FOREIGN PATENT DOCUMENTS

| | | |
|---|---|---|
| EP | 1 527 176 | 1/2007 |
| GB | 2406568 | 4/2005 |
| GB | 2406856 | 4/2005 |
| WO | WO 03/057840 | 7/2003 |
| WO | WO03/059267 A2 * | 7/2003 |
| WO | WO 03/070744 | 8/2003 |
| WO | WO 03/087367 | 10/2003 |
| WO | WO 2004/009794 | 1/2004 |
| WO | WO 2004/009796 | 1/2004 |
| WO | WO 2004/029212 | 4/2004 |

(Continued)

OTHER PUBLICATIONS

Studies conducted in the Biochemistry Department of the School of Optios at the Universidad Compultense de Madrid as filed in the Information Disclosure Statement filed on Oct. 30, 2008 in U.S. Appl. No. 11/574,169.*
Jimenez et al. Invest Opthalmol Vis Sci 2008;49:E-abstract 1643, pp. 1-2.*
Peral Invest Opthalmol Vis Sci 2007;48:E-abstract 4808, pp. 1-2.*
Pintor Invest Opthalmol Vis Sci 2006;47:E-abstract, pp. 1-2.*
Dejinka et al. Molecular Vision 14:997-1005, 2008.*

(Continued)

*Primary Examiner* — Brian Whiteman
(74) *Attorney, Agent, or Firm* — Margaret B. Brivanlou; King & Spalding

(57) ABSTRACT

The invention relates to siNA compositions and methods for the treatment of eye conditions wherein the siNA compound capable of inhibiting the expression of 11 beta-hydroxysteroid dehydrogenase (11 beta-HSD1).

13 Claims, 10 Drawing Sheets

FOREIGN PATENT DOCUMENTS

| | | |
|---|---|---|
| WO | WO 2004/042024 | 5/2004 |
| WO | WO 2004/042046 | 5/2004 |
| WO | WO 2005/040106 | 5/2005 |
| WO | WO 2005/044976 | 5/2005 |
| WO | WO 2005/045037 | 5/2005 |
| WO | WO 2005/076998 | 8/2005 |
| WO | WO 2005/079815 | 9/2005 |
| WO | WO 2006/083945 | 8/2006 |
| WO | WO 2006/084217 | 8/2006 |
| WO | WO 2006/099353 | 9/2006 |

OTHER PUBLICATIONS

Dos Santos et al. Current Pharmaceutical Biotechnology, 6:7-15, 2005.*

Andrieu-Soler et al. Molecular Vision, 12:1334-47, 2006.*

Jimenez et al. Invest. Opthalmol Vis Sci 2007, 48:E-abstract 4809, pp. 1-2.*

Abrams et al., "Comparison of Three Tonometers for Measuring Intraocular Pressure in Rabbits," Invest Ophthalmol Vis Sci. Apr. 1996, 37(5):940-944.

Achenbach et al., Oligonucleotide-Based Knockdown Technologies: Antisense Versus RNA Interference, ChemBioChem., 4, pp. 928-935, 2003.

Ahern et al., "Extracellular Cations Sensitize and Gate Capsaicin Receptor TRPV1 Modulating Pain Signaling," J. Neurosci., May 25, 2005, 25(21), pp. 5109-5116.

Akashi et al., "Suppression of Gene Expression by RNA Interference in Cultured Plant Cells," Antisense Nucleic Acid Drug Dev, 2001, 11(6):359-367.

Amaratunga et al., "Inhibition of Kinesin Synthesis and Rapid Anterograde Axonal Transport in Vivo by An Antisense Oligonucleotide," The Journal of Biological Chemistry, 268(23) pp. 17427-17430, Aug. 15, 1993.

Ambati et al., "Transscleral Delivery of Bioactive Protein to the Choroid and Retina," Investigative Ophthalmology & Visual Science, vol. 41, No. 5, pp. 1186-1191 , Apr. 2000.

Ambion, "The Basics: RNase Control," printout from website <<http://web.archive.org/web/20041207234247>>, dated 2004, retrieved on Sep. 17, 2009.

Banan et al., "The Ins and Outs of RNAi in Mammalian Cells," Current Pharmaceutical Biotechnology, 5, pp. 441-450, 2004.

Banerjee et al., "Control of Developmental Timing by Small Temporal RNAs: a Paradigm for RNA-mediated Regulation of Gene Expression," Bioessays, 2002, 24(2):119-129.

Barar J. et al., "Ocular novel drug delivery impacts of membranes and barriers," *Expert Opin. Drug Deliv.*, 5(5): 567-81, 2008.

Bass, "The Short Answer," Nature, vol. 411, pp. 428-429, 2001.

Basu et al., "Immunological Role of Neuronal Receptor Vanilloid Receptor 1 Expressed on Dendritic Cells," Proc. Natl. Acad. Sci., Apr. 5, 2005, 102(14) pp. 5120-5125.

Baumann et al., "Extracellular Protons Both Increase the Activity and Reduce the conductance of Capsaicin-Gated Channels," J. Neurosci., 2000, 20, RC80, pp. 1-5.

Bhattacharya et al., "Cochlin Deposits in the Trabecular Meshwork of the Glaucomatous DBA/2J mouse," Exp Eye Res., May 2005 80(5):741-744.

Bhattacharya et al., "Proteomics Reveal Cochlin Deposits Associated with Glaucomatous Trabecular Meshwork," J. Biol. Chem., Feb. 2005b, 18;280(7):6080-6084, Epub Dec. 3, 2004.

Bill, "Movement of Albumin and Dextran," Arch. Opthal., vol. 74, pp. 248-252, Aug. 1965.

Bodo et al., "A Hot New Twist to Hair Biology: Involvement of Vanilloid Receptor-1 (VR1/TRPV1) Signaling in Human Hair Growth Control," Am. J. Pathol., Apr. 2005, 166(4), pp. 985-998.

Borrás, "Gene Expression in the Trabecular Meshwork and the Influence of Intraocular Pressure," *Progress in Retinal and Eye Research*, 22, 435-463, 2003.

Bosher et al., "RNA Interference: Genetic Wand and Genetic Watchdog." Nat Cell Biol, 2000, 2(2):E31-6.

Braasch et al., "Novel Antisense and Peptide Nucleic Acid Strategies for Controlling Gene Expression," Biochemistry, 2002, 41(14):4503-4510.

Brock et al., "Effects of Ca2+ and K+ Channel Blockers on Nerve Impulses Recorded from Postganglionic Sympathetic Nerve Terminals," The Journal of Physiology, 1995, 489, pp. 389-402.

Brock et al., "Tetrodotoxin-Resistant Impulses in Single Nociceptor Nerve Terminals in Guinea-Pig Cornea," J. Physiol., Oct. 1998, 512 (Pt. 1), pp. 211-217.

Brummelkamp et al., "A System for Stable Expression of Short Interfering RNAs in Mammalian Cells," Science, American Association for the Advancement of Science, 2002, 296(5567):550-553.

Bujalska et al., "Hexose-6-phosphate Dehydrogenase Confers Oxo-Reductase Activity Upon 11beta-hydroxysteroid Dehydrogenase Type 1," Journal of Molecular Endocrinology, 34(3), pp. 675-684, Jun. 2005.

Busch et al., "Adenylyl Cyclase in Human and Bovine Trabecular Meshwork," Investigative Ophthalmology & Visual Science, 34(10), pp. 3028-3034, Sep. 1993.

Bunce et al., "Associations between the deletion polymorphism of the angiotensin 1-converting enzyme gene and ocular signs of primary open-angle glaucoma," Graefes Arch Clin Exp Ophthalmol., Apr. 2005 243(4):294-299. Epub Oct. 13, 2004.

Caballero et al., "Inefficient Processing of an Olfactomedin-Deficient Myocilin Mutant: Potential Physiological Relevance to Glaucoma," *Biochemical and Biophysical Research Communications*, 282, 662-670, 2001.

Caplen et al., "Specific inhibition of Gene Expression by Small Double Stranded RNAs in Invertebrate and Vertebrate Systems," Proc. Natl. Acad. Sci. USA, 2001,98: 9742-9747.

Caterina et al., "The Capsaicin Receptor: A Heat-Activated Ion Channel in the Pain Pathway," Nature, Oct. 23, 1997, 389(6653), pp. 816-824.

Caterina et al., "The Vanilloid Receptor: A Molecular Gateway to the Pain Pathway," Annu. Rev. Neurosci., 2001, 24, pp. 487-517.

Cho et al., "Small Interfering RNA-Induced TLR3 Activation Inhibits Blood and Lymphatic Vessel Growth," PNAS, pp. 1-6, Dec. 5, 2008.

Christoph et al., "RNA Interference Approaches of Target Validation in Pain Research." International Society for Neurochemistry, 2005, 94(2), p. 142.

Christoph et al., "Silencing of Vanilloid Receptor TRPV1 by RNAi Reduces Neuropathic and Visceral Pain in Vivo," Biochemical and Biophysical Research Communications, 2006, 350, pp. 238-243.

Comes N. and Borrás T, "Functional delivery of synthetic naked siRNA to the human trabecular meshwork in perfused organ cultures," *Molec. Vision*, 13: 1363-74, 2007.

Costagliola et al., "Effect of Oral Losartan Potassium Administration on Intraocular Pressure in Normotensive and Glaucomatous Human Subjects," Exp Eye Res., Aug 2000, 71(2):167-171.

Costagliola et al., "Effect of Oral Captopril (SQ 14225) on Intraocular Pressure in Man," Eur. J. Opthalmol, Jan. 1995, 5(1):19-25.

Crooke et al., "Nucleotides in Ocular Secretions: Their Role in Ocular Physiology," Pharmacology & Therapeutics, 119, pp. 55-73, 2008.

Cullinane et al., "Renin-angiotensin System Expression and Secretory Function in Cultured human Ciliary Cody Nonpigmented Epithelium," Br J Ophthalmol. Jun. 2002, 86(6):6766-83.

Denkert et al., "Induction of G0/G1 Cell Cycle Arrest in Ovarian Carcinoma Cells by the Ant-Inflammatory Drug NS-398, but not by COX-2-Specific RNA Interference," Oncogene, 2003, 22:8653-8661.

Di Marzo et al., "Endovanilloid Signaling in Pain," Curr. Opin. Neurobiol., Aug. 2002, 12(4), pp. 372-379.

Diffen, DNA vs. RNA-Difference and Comparison, retrieved from <<http://www.diffen.com/difference/Dna_vs_Rna>> on May 21, 2009.

Diskin et al., "Detection of Differentially Expressed Glycogenes in Trabecular Meshwork of Eyes with Primary Open-Angle Glaucoma," Investigative Opthalmology & Visual Science, Apr. 2006, 47(4):1491-1499.

Elabashir et al., "Duplexes of 21-Nucleotide RNAs mediate RNA interference in Cultured Mammalian Cells," Nature, May 24, 2001, 411(6836):494-498.
Elbashir et al., "Functional Anatomy of siRNAs for Mediating Efficient RNAi in Drosophila Melanogaster Embryo Lysate," EMBO Journal, vol. 20, No. 23, pp. 6877-6888, 2001.
Elbashir et al., "RNA Interference is Mediated by 21- and 22-Nucleotide RNAs," Genes Dev, 2001, 15(2):188-200.
Elena et al., "Autoradiographic Localization of Beta-Adrenergic Receptors in Rabbit Eye," Investigative Ophthalmology & Visual Science, 28, pp. 1436-1441, Aug. 1987.
Epstein et al., "*Effect of Iodoacetamide Perfusion on Outflow Facility and Metabolism of the Trabecular Meshwork*," Invest. Ophthalmol. Vis. Sci., 625-631, May 1981.
Fattal et al., "Antisense Oligonucleotides, Aptamers and siRNA: Promises for the Treatment of Ocular Disease," Arch. Soc. Esp. Oftalmol, 8(1), pp. 1-4, 2006.
Fattal et al., "Ocular Delivery of Nucleic Acids: Antisense Oligonucleotides, Aptamers and siRNA," Advanced Drug Delivery Reviews, 2006, 58:1203-1223.
Fire et al., "Potent and Specific Genetic Interference by Double Stranded RNA in a *Caenorhabditis elegans*," Nature, 1998, 391(6669):806-11.
Freier et al., "The Ups and Downs of Nucleic Acid Duplex Stability: Structure-Stability Studies on Chemically-Modified DNA:RNA Duplexes," Nucleic Acids Research, 25(22), pp. 4429-4443, 1997.
Garcia-Martinez et al., "Attenuation of Thermal Nociception and Hyperalgesia by VR1 Blockers," Proc. Natl. Acad. Sci., Feb. 19, 2002, 99(4), pp. 2374-2379.
Ge et al., "RNA Interference of Influenza Virus Production by Directly Targeting mRNA for Degradation and Indirectly Inhibiting all Viral RNA Transcription," Proc Natl Acad Sci USA., 2003, 100(5):2718-2723.
Ghate D. and Edelhauser H.F., "Barriers to glaucoma drug delivery," *J. Glaucoma*, 17(2), 147-56, 2008.
Gil et al., "Induction of Apoptosis by the dsRNA-dependent Protein Kinase (PKR): Mechanism of Action," Apoptosis, 2000, 5(2):107-114.
Gonzalez et al., "Genes Upregulated in the Human Trabecular Meshwork in Response to Elevated Intraocular Pressure," Investigative Opthalmology & Visual Science, Feb. 2000, 41(2):352-361.
Gonzalez et al., "Reduction of Capsaicin-Induced Ocular Pain and Neurogenic Inflammation by Calcium Antagonists," Investigative Ophthalmology & Visual Science, 34(12), pp. 3329-3335, Nov. 1993.
Grant et al., "Insulin-Like Growth Factors in Vitreous. Studies in Control and Diabetic Subjects with Neovascularization," Diabetes, 1986, 35, pp. 416-420.
Grosshans et al., "Micro-RNAs: Small is Plentiful," J Cell Bioi, 2002, 156(1):17-21.
Grunweller et al., "Comparison of Different Antisense Strategies in Mammalian Cells Using Locked Nucleic Acids, 2'O-methyl RNA," Nucleic Acids Research, vol. 31, No. 12, pp. 3185-3193, Jun. 15, 2003.
Grunweller et al., "RNA Interference Approaches for Target Validation in Pain Research," Society for Neurochemistry, Journal of Neurochemistry, 94(2), p. 142, 2005.
Hammond et al., "Post-Transcriptional Gene Silencing By Double-Standed RNA," Nature, 2001, 2:110-119.
Hara et al., "Bunazosin, a Selective Alpha1-Adrenoceptor Antagonist, as an Anti-glaucoma Drug: Effects on Ocular Circulation and Retinal Neuronal Damage," Cardiovasc Drug Rev. 2005 Spring;23(1):43-56.
Herkel et al., "Update on Topical Carbonic Anhydrase Inhibitors," Current Opinion in Ophthamology, Apr. 2001, 12(2):88-93.
Hogeboom et al., "Angiotensin Converting Enzyme Inhibiting Therapy is Associated with Lower Vitreous Vascular Endothelial Growth Factor Concentrations in Patients with Proliferative Diabetic Retinopathy," Diabetologia, vol. 45, pp. 203-209, 2002.
Horinouchi et al., "Pharmacological Evaluation of Ocular β-Adrenoceptors in Rabbit by Tissue Segment Binding Method," Life Sciences, 84, pp. 181-187, 2009.

Inokuchi et al., "Vitreous Levels of Insulin-Like Growth Factor-1 in Patients with Proliferative Diabetic Retinopathy," Curr. Eye Res., 2001, 23, pp. 368-371.
Jens Kurreck, "Antisense Technologies," Eur. J. Biochem., 270, pp. 1628-1644, 2003.
Jens Kurreck, "Antisense and RNA Interference Approaches to Target Validation in Pain Research," Current Opinion in Drug Discovery & Development, 7(2), pp. 179-187, 2004.
Jia et al., "TRPV1 Receptor: A Target for the Treatment of Pain, Cough, Airway Disease and Urinary Incontinence," Drug News Perspect., Apr. 2005, 18(13), pp. 165-171.
Kaplan et al., "Aqueous Humor Flow in Unilateral Carotid Stenosis," Journal of Glaucoma, 5, pp. 237-240, 1996.
Khaw et al., "Glaucoma-1: Diagnosis," BMJ, 2004a, 328:97-99.
Khaw et al., "Glaucoma-2: Treatment," BMJ, 2004, 328:156-158.
Kim et al., "Inhibition of Ocular Angiogenesis by Sirna Targeting Vascular Endothelial Growth Factor Pathway Genes Therapeutics Strategy for Herpetic Stromal Keratititis," American Journal of Pathology, Dec. 2004, 165(6):2177-285.
Krohn et al., "Transcorneal Flux of Topical Pilocarpine to the Human Aqueous," Am. J. Ophthalmol., 87(1), pp. 50-56, Jan. 1979, Abstract retrieved from <<http://www.ncbi.nlm.nih.gov/pubmed/434053>> on Nov. 9, 2009.
Krutzfeldt et al., "Silencing of microRNAs in vivo with Antagomirs'," Nature, 2005, 438(7068):685-689.
Kwon et al., "Primary Open-Angle Glaucoma," The New England Journal of Medicine, 360(11), pp. 1113-1124, Mar. 12, 2009.
Liao et al., "Expression of Cell Surface Transmembrane Carbonic Anhydrase Genes CA9 and CA12 in the Human Eye: Overexpression of CA12 (CAXII) in Glaucoma," J. Med. Genet., 40, pp. 257-261, 2003.
Lilja et al., "Development of a Sensory Neuronal Cell Model for the Estimation of Mild Eye Irritation," Altern Lab Anim., Oct. 2004, 32(4), pp. 339-343.
Lograno et al., "Receptor-Responses in Fresh Human Ciliary Muscle," Br. J. Pharmac., 87, pp. 379-385, 1986.
Madsen, "Ocular Finding in 123 Patients with Proliferative Diabetic Retinopathy," Documenta Ophthalmologica, Advances in ophthalmology, May 14, 1971, 29(2):345-349.
Mahato et al., "Modulation of Gene Expression by Antisense and Antigene Oligodeoxynucleotides and Small Interfering RNA," Expert Opinion on Drug Delivery, Jan. 2005, 2(1):3-28.
Meade et al., "Enhancing the Cellular Uptake of siRNA Duplexes Following Noncovalent Packaging with Protein Transduction Domain Peptides," Advanced Drug Delivery Reviews, 60, pp. 530-536, 2008.
Merimee et al., "Insulin-Like Growth Factors. Studies in Diabetics with and without Retinopathy," N. Engl. J. Med., 1983, 309, pp. 527-530.
Meyer-Schwickerath et al., "Vitreous Levels of the Insulin-Like Growth Factors I and II. And the Insulin-like Growth Factor Binding Proteins 2 and 3, Increase in Neovascular Eye Disease—Studies in Nondiabetic and Diabetic Subjects," J. Clin. Invest., 1993, 92(6), pp. 2620-2625.
Miller et al., "Allele-specific Silencing of Dominant Disease Genes," Proceedings of the National Academy of Sciences of USA, Jun. 10, 2003, 100(12):7195-7200.
Mirshahi et al., "The Mineralocorticoid Hormone Receptor and Action in the Eye," Biochem Biophys Res Commun, vol. 219, pp. 150-156, 1996.
Moriyama et al., "Sensitization of TRPV1 by EP1 and IP Reveals Peripheral Nociceptive Mechanism of Prostaglandins," Mol. Pain., Jan. 17, 2005, 1(3), pp. 1-13.
Muratovska et al., "Conjugate for Efficient Delivery of Short Interfering RNA (siRNA) into Mammalian Cells," FEBS Letters, 558, pp. 63-68, 2004.
Nie Y., et al., "The potential therapeutic of siRNA eye drops in ocular diseases," *Bioscience Hypotheses*, 2, 223-25, 2009.
Okabe et al., "Effect of Benzalkonium Chloride on Transscleral Drug Delivery," Investigative Ophthalmology & Visual Science, vol. 46, No. 2, pp. 703-708, Feb. 2005.

Olsen et al., "Human Scleral Permeability: Effects of Age, Cryotherapy, Transscleral Diode Laser, and Surgical Thinning," Investigative Ophthalmology & Visual Science, vol. 36, No. 9. pp. 1893-1903, Aug. 1995.

Osborne et al., "Some Current Ideas on the Pathogenesis and the Role of Neuroprotection in Glaucomatous Optic Neuropathy," Eur J Ophthalmol., Apr. 2003, 13Suppl. 3:S19-26.

Paddison et al., "Short hairpin RNAs (shRNAs) Induce Sequence-Specific Silencing in Mammalian Cells," Genes Dev, 2002, 16(8):948-958.

Pintor et al., "Adenosine Tetraphosphate, $Ap_4$, a Physiological Regulator of Intraocular Pressure in Normotensive Rabbit Eyes," The Journal of Pharmacology and Experimental Therapeutics, vol. 308, No. 2, pp. 468-473, 2004.

Rao et al., "Modulation of Aqueous Humor Outflow Facility by the Rho Kinase-Specific Inhibitor Y-27632," Investigative Opthalmology & Visual Science, Apr. 2001, 42(5): 1029-1037.

Rauz et al., "Expression and Putative Role of 11beta-Hydroxysteriod Dehydrogenase Isozymes Within the Human Eye," Investigative Ophthalmology & Visual Science, 42(9), pp. 2037-2042, 2001.

Rauz et al., "Inhibition of 11beta-hydroxysteriod dehydrogenase type 1 Lowers Intraocular Pressure in Patients with Ocular Hypertension," Q J Med., 96(7), pp. 481-490, Jul. 2003.

Reich et al., "Small Interfering RNA (siRNA) Targeting *VEGF* effectively Inhibits Ocular Neovascularization in a Mouse Model," Molecular Vision, 2003, 9:210-216.

Ruberte et al., "Increased Ocular Levels of IGF-1 in Transgenic Mice Lead to Diabetes-like Eye Disease," J. Clin. Invest., Apr. 2004, 113(8), pp. 1149-1157.

Sakaguchi et al., "Chymase and Angiotensin Converting Enzyme Activities in a Hamster Model of Glaucoma Filtering Surgery," Curr Eye Res., May 2002, 24(5):325-331.

Scherer et al., "Approaches for the Sequence-Specific Knockdown of mRNA," Nat. Biotechnology, 2003, 21(12):1457-1465.

Schubert et al., "Local RNA Target Structure Influences siRNA Efficacy: Systematic Analysis of Intentionally Designed Binding Regions," J. Mol. Biol., 2006, 348, pp. 883-893.

Shah et al., "Oculohypotensive Effect of Angiotensin-Converting Enzyme Inhibitors in Acute and Chronic Models of Glaucoma," J Cardiovasc Pharmacol. Aug. 2000, 36(2):169-175.

Stamer et al., "Isolation and Culture of Human Trabecular Meshwork Cells by Extracellular Matrix Digestion," Current Eye Research, pp. 611-617, Jan. 10, 1995.

Stander et al., "Expression of Vanilloid Receptor Subtype 1 in Cutaneous Sensory Nerve Fibers, Mast Cells, and Epithelial Cells of Appendage Structures," Exp. Dermatol., Mar. 2004, 13(3), pp. 129-139.

Stokes et al., "Distribution of Glucocorticoid and Mineralocorticoid Receptors and 11 β-Hydroxysteroid Dehydrogenases in Human and Rat Ocular Tissues," Invest. Ophthalmol. Vis Sci., 41(7), pp. 1629-1638, Jun. 2000.

Supuran et al., "Carbonic Anhydrates Inhibitors," Medicinal Research Reviews, 23, pp. 146-189, 2003.

Suzuki et al., "'Immunohistochemical Distribution of 11β-hydroxysteroid Dehydrogenase in Human Eye," Mol Cell Endocrinol, vol. 173, pp. 121-125, 2001.

Tan et al., "Recent Developments in Understanding the Pathophysiology of Elevated Intraocular Pressure," Current Opinion in Opthalmology, vol. 17, pp. 168-174, 2006.

Tomlinson, "11Beta-hydroxsteroid Dehydogenase Type I in Human Disease: a Novel Therapeutic Target," Minerva Endocrinologica, 30(1), pp. 37-46, Mar. 2005.

Tuschl et al., "Targeted mRNA degradation by double-stranded RNA in vitro," Genes Dev., 1999, 13(24):3191-3197.

Uprichard et al., The Therapeutic Potential of RNA Interference, FEBS Letters, Oct. 31, 2005 579(26):5996-6007.

U. Herkel et al, Update on topical carbonic anhydrase inhibitors, Curr. Opthalmol., vol. 12 (2), p. 88-93, Apr. 2001, XP002375306.

Valls et al., "Validation of a Device for Transcorneal Drug Permeation Measure," Journal of Pharmaceutical and Biomedical Analysis, 48, pp. 657-663, 2008.

Van Buren et al., "Sensitization and Translocation of TRPV1 by Insulin and IGF-I." Mol. Pain, Apr. 27, 2005, 1(1), p. 17.

Vittal et al., "Changes in Gene Expression by Trabecular Meshword Cells in Response to Mechanical Stretching," Investigative Opthalmology & Visual Science, Aug. 2005, 46(8):2857-2868.

Wang et al., Effect of C5-088, an Angiotensin AT1 Receptor Antagonist, on Intraocular Pressure in Glaucomatous Monkey Eyes, Exp Eye Res., May 2005 80(5):629-632. Epub Jan. 4, 2005.

Wax et al., "Vacuolar $H^+$-ATPase in Ocular Ciliary Epithelium," Proc. Natl. Acad. Sci., vol. 94, pp. 6752-6757, Jun. 1997.

Wetering et al., "Specific Inhibition of Gene Expression Using a Stably Integrated, Inducible Small-Interfering-RNA Vector," EMBO Reports, Jun. 2003, 4(6):609-615.

Wianny et al., "Specific Interference with Gene Function by Double-Stranded RNA in Early Mouse Development," Nat Cell Biol, 2000, 2(2):70-75.

Williams BR, "Role of the Double-Stranded RNA-activated Protein kinase (PKR) in Cell Regulation," Biochem Soc Trans, 1997, 25(2):509-513.

Wirtz et al., "The Genetic Loci of Open-Angle Glaucoma," Ophthalmol. Clin. North Am. 2003 16:505-514.

Wiznerowicz et al., "Conditional Suppression of Cellular Genes: Lentivirus Vector-Mediated Drug-Inducible RNA Interference," Journal of Virology, Aug. 2003, 77(16):8957-8961.

Woodward et al., "The Inflow and Outflow of Anti-Glaucoma Drugs," Trends in Pharmacological Sciences, May 2004, 25(5):238-241.

Xie et al., "Harnessing in vivo siRNA Delivery for Drug Discovery and Therapeutic Development," Drug Discovery Today, Jan. 2006, 11(1-2):6773.

Yang-Feng et al., "Chromosomal Organization of Adrenergic Receptor Genes," PNAS, 1990, 87:1516-1520.

Yang et al., "Early Growth Response Gene 1 Modulates Androgen Receptor Signaling in Prostate Carcinoma Cells," The Journal of Biological Chemistry, 278(41), pp. 39906-39911, 2003.

Office Action dated Jul. 14, 2008 in corresponding U.S. Appl. No. 11/360,305.

Office Action dated Jan. 29, 2009 in corresponding U.S. Appl. No. 11/360,305.

Office Action dated Nov. 12, 2008 in corresponding U.S. Appl. No. 11/574,169.

Final Office Action dated May 8, 2009 in corresponding U.S. Appl. No. 11/574,169.

Office Action dated Nov. 3, 2009 in corresponding U.S. Appl. No. 12/170,078.

Office Action dated Oct. 15, 2009 in corresponding U.S. Appl. No. 12/170,104.

Office Action dated Oct. 15, 2009 in corresponding U.S. Appl. No. 12/170,157.

Office Action dated Oct. 30, 2009 in corresponding U.S. Appl. No. 12/170,116.

Office Action dated Oct. 30, 2009 in corresponding U.S. Appl. No. 12/170,132.

Office Action dated Oct. 19, 2009 in corresponding U.S. Appl. No. 12/170,148.

Office Action dated Dec. 4, 2009 in corresponding U.S. Appl. No. 11/574,169.

Office Action dated Mar. 19, 2010 in corresponding U.S. Appl. No. 12/170,078.

Office Action dated Mar. 22, 2010 in corresponding U.S. Appl. No. 12/170,104.

Office Action dated Mar. 19, 2010 in corresponding U.S. Appl. No. 12/170,116.

Office Action dated Mar. 22, 2010 in corresponding U.S. Appl. No. 12/170,132.

Office Action dated Mar. 22, 2010 in corresponding U.S. Appl. No. 12/170,148.

Office Action dated Mar. 25, 2010 in corresponding U.S. Appl. No. 12/563,530.

Final Office Action dated Jul. 22, 2010 in corresponding U.S. Appl. No. 11/574,169.

Office Action dated Sep. 7, 2010 in corresponding U.S. Appl. No. 11/574,169.

Office Action dated Mar. 22, 2010 in corresponding U.S. Appl. No. 12/170,157.
Office Action dated Sep. 23, 2010 in corresponding U.S. Appl. No. 12/170,078.
Office Action dated Sep. 23, 2010 in corresponding U.S. Appl. No. 12/170,104.
Office Action dated Sep. 23, 2010 in corresponding U.S. Appl. No. 12/170,116.
Office Action dated Sep. 23, 2010 in corresponding U.S. Appl. No. 12/170,132.
Office Action dated Sep. 23, 2010 in corresponding U.S. Appl. No. 12/170,148.
Office Action dated Sep. 23, 2010 in corresponding U.S. Appl. No. 12/170,157.
Hart WM, "Intraocular Pressure," Chapter 8, Adler's Physiology of the Eye: Clinical Application, Mosby-Year Book Inc., $9^{th}$ edition, pp. 248-267, 1992.
Davson H, "The Aqueous Humour and The Intraocular Pressure," Davson's Physiology of the Eye, $5^{th}$ edition. Pergamon Press, pp. 3-95, 1990.
Office Action dated Mar. 19, 2012 in corresponding U.S. Appl. No. 12/170,104.
Office Action dated Mar. 19, 2012 in corresponding U.S. Appl. No. 12/170,116.
Office Action dated Mar. 19, 2012 in corresponding U.S. Appl. No. 12/170,132.
Office Action dated Mar. 19, 2012 in corresponding U.S. Appl. No. 12/170,148.
Office Action dated Mar. 19, 2012 in corresponding U.S. Appl. No. 12/170,157.
Papers filed on Mar. 2, 2012, from opponents in Opposition by Alcon Research, Ltd. against Australian Patent Application No. 2005276245 in the name of Sylentis SAU.

* cited by examiner

Figure 1

| Accession number | Definition |
|---|---|
| NM_005525 | Homo sapiens hydroxysteroid (11-beta) dehydrogenase 1 (HSD11B1), transcript variant 1, mRNA |
| NM_181755 | Homo sapiens hydroxysteroid (11-beta) dehydrogenase 1 (HSD11B1), transcript variant 2, mRNA |

Figure 2A

| | Hydroxysteroid (11-beta) dehydrogenase 1 (HSD11B1) |
|---|---|
| SEQ ID 1 | AAAATATCTCCTCCCCATT |
| SEQ ID 2 | AAATATCTCCTCCCCATTC |
| SEQ ID 3 | AATATCTCCTCCCCATTCT |
| SEQ ID 4 | ATATCTCCTCCCCATTCTG |
| SEQ ID 5 | TATCTCCTCCCCATTCTGG |
| SEQ ID 6 | ACGAGGAATTCAGACCAGA |
| SEQ ID 7 | CGAGGAATTCAGACCAGAG |
| SEQ ID 8 | TTCAGACCAGAGATGCTCC |
| SEQ ID 9 | GGAAAGAAAGTGATTGTCA |
| SEQ ID 10 | AGAAAGTGATTGTCACAGG |
| SEQ ID 11 | GAAAGTGATTGTCACAGGG |
| SEQ ID 12 | AGTGATTGTCACAGGGGCC |
| SEQ ID 13 | GTGATTGTCACAGGGGCCA |
| SEQ ID 14 | AGGGATCGGAAGAGAGATG |
| SEQ ID 15 | GGGATCGGAAGAGAGATGG |
| SEQ ID 16 | GAGAGATGGCTTATCATCT |
| SEQ ID 17 | GATGGGAGCCCATGTGGTG |
| SEQ ID 18 | AAGAAACTCTACAGAAGGT |
| SEQ ID 19 | AGAAACTCTACAGAAGGTG |

Figure 2B

| SEQ ID 20 | GAAACTCTACAGAAGGTGG |
| SEQ ID 21 | ACTCTACAGAAGGTGGTAT |
| SEQ ID 22 | CTCTACAGAAGGTGGTATC |
| SEQ ID 23 | GGTGGTATCCCACTGCCTG |
| SEQ ID 24 | GACATGACCTTCGCAGAGC |
| SEQ ID 25 | TTTGTTGCCCAAGCAGGAA |
| SEQ ID 26 | GCAGGAAAGCTCATGGGAG |
| SEQ ID 27 | AGCTCATGGGAGGACTAGA |
| SEQ ID 28 | GCTCATGGGAGGACTAGAC |
| SEQ ID 29 | CCACATCACCAACACTTCT |
| SEQ ID 30 | AAGCATGGAAGTCAACTTC |
| SEQ ID 31 | AGCATGGAAGTCAACTTCC |
| SEQ ID 32 | GCATGGAAGTCAACTTCCT |
| SEQ ID 33 | GTCAACTTCCTCAGTTACG |
| SEQ ID 34 | CTTCCTCAGTTACGTGGTC |
| SEQ ID 35 | GCAGAGCAATGGAAGCATT |
| SEQ ID 36 | TGGAAGCATTGTTGTCGTC |
| SEQ ID 37 | GCATTGTTGTCGTCTCCTC |
| SEQ ID 38 | AGTGGCTTATCCAATGGTT |
| SEQ ID 39 | GTGGCTTATCCAATGGTTG |
| SEQ ID 40 | TGGTTGCTGCCTATTCTGC |
| SEQ ID 41 | GCAAGTTTGCTTTGGATGG |

Figure 2C

| SEQ ID 42 | GTTTGCTTTGGATGGGTTC |
| --- | --- |
| SEQ ID 43 | AGGAATATTCAGTGTCCAG |
| SEQ ID 44 | GGAATATTCAGTGTCCAGG |
| SEQ ID 45 | TATTCAGTGTCCAGGGTCA |
| SEQ ID 46 | TGTATCAATCACTCTCTGT |
| SEQ ID 47 | TCACTCTGTGTTCTTGG |
| SEQ ID 48 | ACAGCCATGAAGGCAGTTT |
| SEQ ID 49 | CAGCCATGAAGGCAGTTTC |
| SEQ ID 50 | GGCAGTTTCTGGGATAGTC |
| SEQ ID 51 | GCAGCTCCAAAGGAGGAAT |
| SEQ ID 52 | AGGAGGAATGTGCCCTGGA |
| SEQ ID 53 | GGAGGAATGTGCCCTGGAG |
| SEQ ID 54 | TGTGCCCTGGAGATCATCA |
| SEQ ID 55 | GAAGTGTATTATGACAGCT |
| SEQ ID 56 | GTGTATTATGACAGCTCAC |
| SEQ ID 57 | ATCCATGCAGGAAGATCCT |
| SEQ ID 58 | TCCATGCAGGAAGATCCTG |
| SEQ ID 59 | GATCCTGGAATTTCTCTAC |
| SEQ ID 60 | TTTCTCTACTCAACGAGCT |
| SEQ ID 61 | CGAGCTATAATATGGACAG |

| Hydroxysteroid (11-beta) dehydrogenase 1 (HSD11B1) | |
|---|---|
| SEQ ID 62 | 5' AAAAUAUCUCCUCCCCAUU 3'<br>\|\|\|\|\|\|\|\|\|\|\|\|\|\|\|\|\|\|\|<br>3' UUUUAUAGAGGAGGGGUAA 5' |
| SEQ ID 63 | 5' AAAUAUCUCCUCCCCAUUC 3'<br>\|\|\|\|\|\|\|\|\|\|\|\|\|\|\|\|\|\|\|<br>3' UUUAUAGAGGAGGGGUAAG 5' |
| SEQ ID 64 | 5' AAUAUCUCCUCCCCAUUCU 3'<br>\|\|\|\|\|\|\|\|\|\|\|\|\|\|\|\|\|\|\|<br>3' UUAUAGAGGAGGGGUAAGA 5' |
| SEQ ID 65 | 5' AUAUCUCCUCCCCAUUCUG 3'<br>\|\|\|\|\|\|\|\|\|\|\|\|\|\|\|\|\|\|\|<br>3' UAUAGAGGAGGGGUAAGAC 5' |
| SEQ ID 66 | 5' UAUCUCCUCCCCAUUCUGG 3'<br>\|\|\|\|\|\|\|\|\|\|\|\|\|\|\|\|\|\|\|<br>3' AUAGAGGAGGGGUAAGACC 5' |
| SEQ ID 67 | 5' ACGAGGAAUUCAGACCAGA 3'<br>\|\|\|\|\|\|\|\|\|\|\|\|\|\|\|\|\|\|\|<br>3' UGCUCCUUAAGUCUGGUCU 5' |
| SEQ ID 68 | 5' CGAGGAAUUCAGACCAGAG 3'<br>\|\|\|\|\|\|\|\|\|\|\|\|\|\|\|\|\|\|\|<br>3' GCUCCUUAAGUCUGGUCUC 5' |
| SEQ ID 69 | 5' UUCAGACCAGAGAUGCUCC 3'<br>\|\|\|\|\|\|\|\|\|\|\|\|\|\|\|\|\|\|\|<br>3' AAGUCUGGUCUCUACGAGG 5' |
| SEQ ID 70 | 5' GGAAAGAAAGUGAUUGUCA 3'<br>\|\|\|\|\|\|\|\|\|\|\|\|\|\|\|\|\|\|\|<br>3' CCUUUCUUUCACUAACAGU 5' |
| SEQ ID 71 | 5' AGAAAGUGAUUGUCACAGG 3'<br>\|\|\|\|\|\|\|\|\|\|\|\|\|\|\|\|\|\|\|<br>3' UCUUUCACUAACAGUGUCC 5' |
| SEQ ID 72 | 5' GAAAGUGAUUGUCACAGGG 3'<br>\|\|\|\|\|\|\|\|\|\|\|\|\|\|\|\|\|\|\|<br>3' CUUUCACUAACAGUGUCCC 5' |
| SEQ ID 73 | 5' AGUGAUUGUCACAGGGGCC 3'<br>\|\|\|\|\|\|\|\|\|\|\|\|\|\|\|\|\|\|\|<br>3' UCACUAACAGUGUCCCCGG 5' |
| SEQ ID 74 | 5' GUGAUUGUCACAGGGGCCA 3'<br>\|\|\|\|\|\|\|\|\|\|\|\|\|\|\|\|\|\|\|<br>3' CACUAACAGUGUCCCCGGU 5' |
| SEQ ID 75 | 5' AGGGAUCGGAAGAGAGAUG 3'<br>\|\|\|\|\|\|\|\|\|\|\|\|\|\|\|\|\|\|\|<br>3' UCCCUAGCCUUCUCUCUAC 5' |
| SEQ ID 76 | 5' GGGAUCGGAAGAGAGAUGG 3'<br>\|\|\|\|\|\|\|\|\|\|\|\|\|\|\|\|\|\|\|<br>3' CCCUAGCCUUCUCUCUACC 5' |
| SEQ ID 77 | 5' GAGAGAUGGCUUAUCAUCU 3'<br>\|\|\|\|\|\|\|\|\|\|\|\|\|\|\|\|\|\|\|<br>3' CUCUCUACCGAAUAGUAGA 5' |
| SEQ ID 78 | 5' GAUGGGAGCCCAUGUGGUG 3'<br>\|\|\|\|\|\|\|\|\|\|\|\|\|\|\|\|\|\|\| |

Figure 3A

```
                3' CUACCCUCGGGUACACCAC 5'
                5' AAGAAACUCUACAGAAGGU 3'
SEQ ID 79          |||||||||||||||||||
                3' UUCUUUGAGAUGUCUUCCA 5'
                5' AGAAACUCUACAGAAGGUG 3'
SEQ ID 90          |||||||||||||||||||
                3' UCUUUGAGAUGUCUUCCAC 5'
                5' GAAACUCUACAGAAGGUGG 3'
SEQ ID 91          |||||||||||||||||||
                3' CUUUGAGAUGUCUUCCACC 5'
                5' ACUCUACAGAAGGUGGUAU 3'
SEQ ID 92          |||||||||||||||||||
                3' UGAGAUGUCUUCCACCAUA 5'
                5' CUCUACAGAAGGUGGUAUC 3'
SEQ ID 93          |||||||||||||||||||
                3' GAGAUGUCUUCCACCAUAG 5'
                5' GGUGGUAUCCCACUGCCUG 3'
SEQ ID 94          |||||||||||||||||||
                3' CCACCAUAGGGUGACGGAC 5'
                5' GACAUGACCUUCGCAGAGC 3'
SEQ ID 95          |||||||||||||||||||
                3' CUGUACUGGAAGCGUCUCG 5'
                5' UUUGUUGCCCAAGCAGGAA 3'
SEQ ID 96          |||||||||||||||||||
                3' AAACAACGGGUUCGUCCUU 5'
                5' GCAGGAAAGCUCAUGGGAG 3'
SEQ ID 97          |||||||||||||||||||
                3' CGUCCUUUCGAGUACCCUC 5'
                5' AGCUCAUGGGAGGACUAGA 3'
SEQ ID 98          |||||||||||||||||||
                3' UCGAGUACCCUCCUGAUCU 5'
                5' GCUCAUGGGAGGACUAGAC 3'
SEQ ID 99          |||||||||||||||||||
                3' CGAGUACCCUCCUGAUCUG 5'
                5' CCACAUCACCAACACUUCU 3'
                   |||||||||||||||||||
SEQ ID 100      3' GGUGUAGUGGUUGUGAAGA 5'

5' AAGCAUGGAAGUCAACUUC 3'
                   |||||||||||||||||||
SEQ ID 101      3' UUCGUACCUUCAGUUGAAG 5'
                5' AGCAUGGAAGUCAACUUCC 3'
SEQ ID 102         |||||||||||||||||||
                3' UCGUACCUUCAGUUGAAGG 5'
                5' GCAUGGAAGUCAACUUCCU 3'
SEQ ID 103         |||||||||||||||||||
                3' CGUACCUUCAGUUGAAGGA 5'
                5' GUCAACUCCUCAGUUACG 3'
SEQ ID 104         |||||||||||||||||||
                3' CAGUUGAAGGAGUCAAUGC 5'
                5' CUUCCUCAGUUACGUGGUC 3'
SEQ ID 105         |||||||||||||||||||
                3' GAAGGAGUCAAUGCACCAG 5'
                5' GCAGAGCAAUGGAAGCAUU 3'
SEQ ID 106         |||||||||||||||||||
                3' CGUCUCGUUACCUUCGUAA 5'
```

Figure 3B

```
SEQ ID 107    5' UGGAAGCAUUGUUGUCGUC 3'
              |||||||||||||||||||
              3' ACCUUCGUAACAACAGCAG 5'
SEQ ID 108    5' GCAUUGUUGUCGUCUCCUC 3'
              |||||||||||||||||||
              3' CGUAACAACAGCAGAGGAG 5'
SEQ ID 109    5' AGUGGCUUAUCCAAUGGUU 3'
              |||||||||||||||||||
              3' UCACCGAAUAGGUUACCAA 5'
SEQ ID 110    5' GUGGCUUAUCCAAUGGUUG 3'
              |||||||||||||||||||
              3' CACCGAAUAGGUUACCAAC 5'
SEQ ID 111    5' UGGUUGCUGCCUAUUCUGC 3'
              |||||||||||||||||||
              3' ACCAACGACGGAUAAGACG 5'
SEQ ID 112    5' GCAAGUUUGCUUUGGAUGG 3'
              |||||||||||||||||||
              3' CGUUCAAACGAAACCUACC 5'
SEQ ID 113    5' GUUUGCUUUGGAUGGGUUC 3'
              |||||||||||||||||||
              3' CAAACGAAACCUACCCAAG 5'
SEQ ID 114    5' AGGAAUAUUCAGUGUCCAG 3'
              |||||||||||||||||||
              3' UCCUUAUAAGUCACAGGUC 5'
SEQ ID 115    5' GGAAUAUUCAGUGUCCAGG 3'
              |||||||||||||||||||
              3' CCUUAUAAGUCACAGGUCC 5'

SEQ ID 116    5' UAUUCAGUGUCCAGGGUCA 3'
              |||||||||||||||||||
              3' AUAAGUCACAGGUCCCAGU 5'
SEQ ID 117    5' UGUAUCAAUCACUCUCUGU 3'
              |||||||||||||||||||
              3' ACAUAGUUAGUGAGAGACA 5'
SEQ ID 118    5' UCACUCUCUGUGUUCUUGG 3'
              |||||||||||||||||||
              3' AGUGAGAGACACAAGAACC 5'
SEQ ID 119    5' ACAGCCAUGAAGGCAGUUU 3'
              |||||||||||||||||||
              3' UGUCGGUACUUCCGUCAAA 5'
SEQ ID 120    5' CAGCCAUGAAGGCAGUUUC 3'
              |||||||||||||||||||
              3' GUCGGUACUUCCGUCAAAG 5'
SEQ ID 121    5' GGCAGUUUCUGGGAUAGUC 3'
              |||||||||||||||||||
              3' CCGUCAAAGACCCUAUCAG 5'
SEQ ID 122    5' GCAGCUCCAAAGGAGGAAU 3'
              |||||||||||||||||||
              3' CGUCGAGGUUUCCUCCUUA 5'
SEQ ID 123    5' AGGAGGAAUGUGCCCUGGA 3'
              |||||||||||||||||||
              3' UCCUCCUUACACGGGACCU 5'
SEQ ID 124    5' GGAGGAAUGUGCCCUGGAG 3'
              |||||||||||||||||||
              3' CCUCCUUACACGGGACCUC 5'
SEQ ID 125    5' UGUGCCCUGGAGAUCAUCA 3'
```

Figure 3C

SEQ ID 126
```
                3' ACACGGGACCUCUAGUAGU 5'
                5' GAAGUGUAUUAUGACAGCU 3'
                   ||||||||||||||||||
                3' CUUCACAUAAUACUGUCGA 5'
```

SEQ ID 127
```
                5' GUGUAUUAUGACAGCUCAC 3'
                   ||||||||||||||||||
                3' CACAUAAUACUGUCGAGUG 5'
```

SEQ ID 128
```
                5' AUCCAUGCAGGAAGAUCCU 3'
                   ||||||||||||||||||
                3' UAGGUACGUCCUUCUAGGA 5'
```

SEQ ID 129
```
                5' UCCAUGCAGGAAGAUCCUG 3'
                   ||||||||||||||||||
                3' AGGUACGUCCUUCUAGGAC 5'
```

SEQ ID 130
```
                5' GAUCCUGGAAUUUCUCUAC 3'
                   ||||||||||||||||||
                3' CUAGGACCUUAAAGAGAUG 5'
```

SEQ ID 131
```
                5' UUUCUCUACUCAACGAGCU 3'
                   ||||||||||||||||||
                3' AAAGAGAUGAGUUGCUCGA 5'
```

SEQ ID 132
```
                5' CGAGCUAUAAUAUGGACAG 3'
                   ||||||||||||||||||
                3' GCUCGAUAUUAUACCUGUC 5'
```

Figure 3D

SEQUENCE LISTING

<160> NUMBER OF SEQ ID NOS: 134

<210> SEQ ID NO 1
<211> LENGTH: 19
<212> TYPE: DNA
<213> ORGANISM: Homo sapiens

<400> SEQUENCE: 1
aaaatatctc ctccccatt                                                    19

<210> SEQ ID NO 2
<211> LENGTH: 19
<212> TYPE: DNA
<213> ORGANISM: Homo sapiens

<400> SEQUENCE: 2
aaatatctcc tccccattc                                                19

<210> SEQ ID NO 3
<211> LENGTH: 19
<212> TYPE: DNA
<213> ORGANISM: Homo sapiens

<400> SEQUENCE: 3
aatatctcct ccccattct                                                19

<210> SEQ ID NO 4
<211> LENGTH: 19
<212> TYPE: DNA
<213> ORGANISM: Homo sapiens

<400> SEQUENCE: 4
atatctcctc cccattctg                                                19

<210> SEQ ID NO 5
<211> LENGTH: 19
<212> TYPE: DNA
<213> ORGANISM: Homo sapiens

<400> SEQUENCE: 5
tatctcctcc ccattctgg                                                19

<210> SEQ ID NO 6
<211> LENGTH: 19
<212> TYPE: DNA
<213> ORGANISM: Homo sapiens

<400> SEQUENCE: 6
acgaggaatt cagaccaga                                                19

<210> SEQ ID NO 7
<211> LENGTH: 19
<212> TYPE: DNA
<213> ORGANISM: Homo sapiens

<400> SEQUENCE: 7
cgaggaattc agaccagag                                                19

<210> SEQ ID NO 8
<211> LENGTH: 19
<212> TYPE: DNA
<213> ORGANISM: Homo sapiens

<400> SEQUENCE: 8
ttcagaccag agatgctcc                                                19

<210> SEQ ID NO 9
<211> LENGTH: 19
<212> TYPE: DNA
<213> ORGANISM: Homo sapiens

<400> SEQUENCE: 9
ggaaagaaag tgattgtca                                                19

<210> SEQ ID NO 10
<211> LENGTH: 19
<212> TYPE: DNA
<213> ORGANISM: Homo sapiens

```
<400> SEQUENCE: 10
agaaagtgat tgtcacagg                                                        19

<210> SEQ ID NO 11
<211> LENGTH: 19
<212> TYPE: DNA
<213> ORGANISM: Homo sapiens

<400> SEQUENCE: 11
gaaagtgatt gtcacaggg                                                        19

<210> SEQ ID NO 12
<211> LENGTH: 19
<212> TYPE: DNA
<213> ORGANISM: Homo sapiens

<400> SEQUENCE: 12
agtgattgtc acagggcc                                                         19

<210> SEQ ID NO 13
<211> LENGTH: 19
<212> TYPE: DNA
<213> ORGANISM: Homo sapiens

<400> SEQUENCE: 13
gtgattgtca caggggcca                                                        19

<210> SEQ ID NO 14
<211> LENGTH: 19
<212> TYPE: DNA
<213> ORGANISM: Homo sapiens

<400> SEQUENCE: 14
agggatcgga agagagatg                                                        19

<210> SEQ ID NO 15
<211> LENGTH: 19
<212> TYPE: DNA
<213> ORGANISM: Homo sapiens

<400> SEQUENCE: 15
gggatcggaa gagagatgg                                                        19

<210> SEQ ID NO 16
<211> LENGTH: 19
<212> TYPE: DNA
<213> ORGANISM: Homo sapiens

<400> SEQUENCE: 16
gagagatggc ttatcatct                                                        19

<210> SEQ ID NO 17
<211> LENGTH: 19
<212> TYPE: DNA
<213> ORGANISM: Homo sapiens

<400> SEQUENCE: 17
gatgggagcc catgtggtg                                                        19

<210> SEQ ID NO 18
<211> LENGTH: 19
<212> TYPE: DNA
<213> ORGANISM: Homo sapiens
```

-continued

```
<400> SEQUENCE: 18
aagaaactct acagaaggt                                                19

<210> SEQ ID NO 19
<211> LENGTH: 19
<212> TYPE: DNA
<213> ORGANISM: Homo sapiens

<400> SEQUENCE: 19
agaaactcta cagaaggtg                                                19

<210> SEQ ID NO 20
<211> LENGTH: 19
<212> TYPE: DNA
<213> ORGANISM: Homo sapiens

<400> SEQUENCE: 20
gaaactctac agaaggtgg                                                19

<210> SEQ ID NO 21
<211> LENGTH: 19
<212> TYPE: DNA
<213> ORGANISM: Homo sapiens

<400> SEQUENCE: 21
actctacaga aggtggtat                                                19

<210> SEQ ID NO 22
<211> LENGTH: 19
<212> TYPE: DNA
<213> ORGANISM: Homo sapiens

<400> SEQUENCE: 22
ctctacagaa ggtggtatc                                                19

<210> SEQ ID NO 23
<211> LENGTH: 19
<212> TYPE: DNA
<213> ORGANISM: Homo sapiens

<400> SEQUENCE: 23
ggtggtatcc cactgcctg                                                19

<210> SEQ ID NO 24
<211> LENGTH: 19
<212> TYPE: DNA
<213> ORGANISM: Homo sapiens

<400> SEQUENCE: 24
gacatgacct tcgcagagc                                                19

<210> SEQ ID NO 25
<211> LENGTH: 19
<212> TYPE: DNA
<213> ORGANISM: Homo sapiens

<400> SEQUENCE: 25
tttgttgccc aagcaggaa                                                19

<210> SEQ ID NO 26
<211> LENGTH: 19
<212> TYPE: DNA
<213> ORGANISM: Homo sapiens
```

<400> SEQUENCE: 26
gcaggaaagc tcatgggag                                                      19

<210> SEQ ID NO 27
<211> LENGTH: 19
<212> TYPE: DNA
<213> ORGANISM: Homo sapiens

<400> SEQUENCE: 27
agctcatggg aggactaga                                                      19

<210> SEQ ID NO 28
<211> LENGTH: 19
<212> TYPE: DNA
<213> ORGANISM: Homo sapiens

<400> SEQUENCE: 28
gctcatggga ggactagac                                                      19

<210> SEQ ID NO 29
<211> LENGTH: 19
<212> TYPE: DNA
<213> ORGANISM: Homo sapiens

<400> SEQUENCE: 29
ccacatcacc aacacttct                                                      19

<210> SEQ ID NO 30
<211> LENGTH: 19
<212> TYPE: DNA
<213> ORGANISM: Homo sapiens

<400> SEQUENCE: 30
aagcatggaa gtcaacttc                                                      19

<210> SEQ ID NO 31
<211> LENGTH: 19
<212> TYPE: DNA
<213> ORGANISM: Homo sapiens

<400> SEQUENCE: 31
agcatggaag tcaacttcc                                                      19

<210> SEQ ID NO 32
<211> LENGTH: 19
<212> TYPE: DNA
<213> ORGANISM: Homo sapiens

<400> SEQUENCE: 32
gcatggaagt caacttcct                                                      19

<210> SEQ ID NO 33
<211> LENGTH: 19
<212> TYPE: DNA
<213> ORGANISM: Homo sapiens

<400> SEQUENCE: 33
gtcaacttcc tcagttacg                                                      19

<210> SEQ ID NO 34
<211> LENGTH: 19
<212> TYPE: DNA
<213> ORGANISM: Homo sapiens

<400> SEQUENCE: 34
cttcctcagt tacgtggtc                                                    19

<210> SEQ ID NO 35
<211> LENGTH: 19
<212> TYPE: DNA
<213> ORGANISM: Homo sapiens

<400> SEQUENCE: 35
gcagagcaat ggaagcatt                                                    19

<210> SEQ ID NO 36
<211> LENGTH: 19
<212> TYPE: DNA
<213> ORGANISM: Homo sapiens

<400> SEQUENCE: 36
tggaagcatt gttgtcgtc                                                    19

<210> SEQ ID NO 37
<211> LENGTH: 19
<212> TYPE: DNA
<213> ORGANISM: Homo sapiens

<400> SEQUENCE: 37
gcattgttgt cgtctcctc                                                    19

<210> SEQ ID NO 38
<211> LENGTH: 19
<212> TYPE: DNA
<213> ORGANISM: Homo sapiens

<400> SEQUENCE: 38
agtggcttat ccaatggtt                                                    19

<210> SEQ ID NO 39
<211> LENGTH: 19
<212> TYPE: DNA
<213> ORGANISM: Homo sapiens

<400> SEQUENCE: 39
gtggcttatc caatggttg                                                    19

<210> SEQ ID NO 40
<211> LENGTH: 19
<212> TYPE: DNA
<213> ORGANISM: Homo sapiens

<400> SEQUENCE: 40
tggttgctgc ctattctgc                                                    19

<210> SEQ ID NO 41
<211> LENGTH: 19
<212> TYPE: DNA
<213> ORGANISM: Homo sapiens

<400> SEQUENCE: 41
gcaagtttgc tttggatgg                                                    19

<210> SEQ ID NO 42
<211> LENGTH: 19
<212> TYPE: DNA
<213> ORGANISM: Homo sapiens

```
<400> SEQUENCE: 42
gtttgctttg gatgggttc                                              19

<210> SEQ ID NO 43
<211> LENGTH: 19
<212> TYPE: DNA
<213> ORGANISM: Homo sapiens

<400> SEQUENCE: 43
aggaatattc agtgtccag                                              19

<210> SEQ ID NO 44
<211> LENGTH: 19
<212> TYPE: DNA
<213> ORGANISM: Homo sapiens

<400> SEQUENCE: 44
ggaatattca gtgtccagg                                              19

<210> SEQ ID NO 45
<211> LENGTH: 19
<212> TYPE: DNA
<213> ORGANISM: Homo sapiens

<400> SEQUENCE: 45
tattcagtgt ccagggtca                                              19

<210> SEQ ID NO 46
<211> LENGTH: 19
<212> TYPE: DNA
<213> ORGANISM: Homo sapiens

<400> SEQUENCE: 46
tgtatcaatc actctctgt                                              19

<210> SEQ ID NO 47
<211> LENGTH: 19
<212> TYPE: DNA
<213> ORGANISM: Homo sapiens

<400> SEQUENCE: 47
tcactctctg tgttcttgg                                              19

<210> SEQ ID NO 48
<211> LENGTH: 19
<212> TYPE: DNA
<213> ORGANISM: Homo sapiens

<400> SEQUENCE: 48
acagccatga aggcagttt                                              19

<210> SEQ ID NO 49
<211> LENGTH: 19
<212> TYPE: DNA
<213> ORGANISM: Homo sapiens

<400> SEQUENCE: 49
cagccatgaa ggcagtttc                                              19

<210> SEQ ID NO 50
<211> LENGTH: 19
<212> TYPE: DNA
<213> ORGANISM: Homo sapiens
```

```
<400> SEQUENCE: 50
ggcagtttct gggatagtc                                                19

<210> SEQ ID NO 51
<211> LENGTH: 19
<212> TYPE: DNA
<213> ORGANISM: Homo sapiens

<400> SEQUENCE: 51
gcagctccaa aggaggaat                                                19

<210> SEQ ID NO 52
<211> LENGTH: 19
<212> TYPE: DNA
<213> ORGANISM: Homo sapiens

<400> SEQUENCE: 52
aggaggaatg tgccctgga                                                19

<210> SEQ ID NO 53
<211> LENGTH: 19
<212> TYPE: DNA
<213> ORGANISM: Homo sapiens

<400> SEQUENCE: 53
ggaggaatgt gccctggag                                                19

<210> SEQ ID NO 54
<211> LENGTH: 19
<212> TYPE: DNA
<213> ORGANISM: Homo sapiens

<400> SEQUENCE: 54
tgtgccctgg agatcatca                                                19

<210> SEQ ID NO 55
<211> LENGTH: 19
<212> TYPE: DNA
<213> ORGANISM: Homo sapiens

<400> SEQUENCE: 55
gaagtgtatt atgacagct                                                19

<210> SEQ ID NO 56
<211> LENGTH: 19
<212> TYPE: DNA
<213> ORGANISM: Homo sapiens

<400> SEQUENCE: 56
gtgtattatg acagctcac                                                19

<210> SEQ ID NO 57
<211> LENGTH: 19
<212> TYPE: DNA
<213> ORGANISM: Homo sapiens

<400> SEQUENCE: 57
atccatgcag gaagatcct                                                19

<210> SEQ ID NO 58
<211> LENGTH: 19
<212> TYPE: DNA
<213> ORGANISM: Homo sapiens
```

-continued

<400> SEQUENCE: 58
tccatgcagg aagatcctg                                                19

<210> SEQ ID NO 59
<211> LENGTH: 19
<212> TYPE: DNA
<213> ORGANISM: Homo sapiens

<400> SEQUENCE: 59
gatcctggaa tttctctac                                                19

<210> SEQ ID NO 60
<211> LENGTH: 19
<212> TYPE: DNA
<213> ORGANISM: Homo sapiens

<400> SEQUENCE: 60
tttctctact caacgagct                                                19

<210> SEQ ID NO 61
<211> LENGTH: 19
<212> TYPE: DNA
<213> ORGANISM: Homo sapiens

<400> SEQUENCE: 61
cgagctataa tatggacag                                                19

<210> SEQ ID NO 62
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 1

<400> SEQUENCE: 62
uuuuauagag gagggguaa                                                19

<210> SEQ ID NO 63
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 2

<400> SEQUENCE: 63
uuuauagagg aggggguaag                                               19

<210> SEQ ID NO 64
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 3

<400> SEQUENCE: 64
uuauagagga ggggguaaga                                               19

<210> SEQ ID NO 65
<211> LENGTH: 19
<212> TYPE: RNA
<213> ORGANISM: Homo sapiens

```
<220> FEATURE:
<221> NAME/KEY: misc_feature
<223> OTHER INFORMATION: RNA SEQUENCE COMPLEMENTARY TO SEQ 4

<400> SEQUENCE: 65
uauagaggag ggguaagac                                                19

<210> SEQ ID NO 66
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 5

<400> SEQUENCE: 66
auagaggagg gguaagacc                                                19

<210> SEQ ID NO 67
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 6

<400> SEQUENCE: 67
ugcuccuuaa gucuggucu                                                19

<210> SEQ ID NO 68
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 7

<400> SEQUENCE: 68
gcuccuuaag ucuggucuc                                                19

<210> SEQ ID NO 69
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 8

<400> SEQUENCE: 69 aagucgguc ucuacgagg                                                 19

<210> SEQ ID NO 70
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 9

<400> SEQUENCE: 70
ccuuucuuuc acuaacagu                                                19

<210> SEQ ID NO 71
<211> LENGTH: 19
<212> TYPE: RNA
<213> ORGANISM: Homo sapiens
```

```
<220> FEATURE:
<221> NAME/KEY: misc_feature
<223> OTHER INFORMATION: RNA SEQUENCE COMPLEMENTARY TO SEQ 10

<400> SEQUENCE: 71
ucuuucacua acagugucc                                                    19

<210> SEQ ID NO 72
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 11

<400> SEQUENCE: 72
cuuucacuaa cagugsuccc                                                   19

<210> SEQ ID NO 73
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 12

<400> SEQUENCE: 73
ucacuaacag ugsccccgg                                                    19

<210> SEQ ID NO 74
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 13

<400> SEQUENCE: 74
cacuaacagu gucccggu                                                     19

<210> SEQ ID NO 75
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 14

<400> SEQUENCE: 75
ucccuagccu ucucucuac                                                    19

<210> SEQ ID NO 76
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 15

<400> SEQUENCE: 76
cccuagccuu cucucuacc                                                    19

<210> SEQ ID NO 77
<211> LENGTH: 19
<212> TYPE: RNA
<213> ORGANISM: Homo sapiens
```

```
<220> FEATURE:
<221> NAME/KEY: misc_feature
<223> OTHER INFORMATION: RNA SEQUENCE COMPLEMENTARY TO SEQ 16

<400> SEQUENCE: 77
cucucuaccg aauaguaga                                                19

<210> SEQ ID NO 78
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 17

<400> SEQUENCE: 78
cuacccucgg guacaccac                                                19

<210> SEQ ID NO 79
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 18

<400> SEQUENCE: 79
uucuuugaga ugucuucca                                                19

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000
```

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 19

<400> SEQUENCE: 90
ucuuugagau gucuuccac                                                    19

<210> SEQ ID NO 91
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 20

<400> SEQUENCE: 91
cuuugagaug ucuuccacc                                                    19

<210> SEQ ID NO 92
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 21

<400> SEQUENCE: 92
ugagaugucu uccaccaua                                                    19

<210> SEQ ID NO 93
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 22

<400> SEQUENCE: 93
gagaugucuu ccaccauag                                                    19

```
<210> SEQ ID NO 94
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 23

<400> SEQUENCE: 94
ccaccauagg gugacggac                                                    19

<210> SEQ ID NO 95
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 24

<400> SEQUENCE: 95
cuguacugga agcgucucg                                                    19

<210> SEQ ID NO 96
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 25

<400> SEQUENCE: 96
aaacaacggg uucguccuu                                                    19

<210> SEQ ID NO 97
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 26

<400> SEQUENCE: 97
cguccuuucg aguacccuc                                                    19

<210> SEQ ID NO 98
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 27

<400> SEQUENCE: 98
ucgaguaccc uccugaucu                                                    19

<210> SEQ ID NO 99
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 28

<400> SEQUENCE: 99
cgaguacccu ccugaucug                                                    19
```

-continued

```
<210> SEQ ID NO 100
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 29

<400> SEQUENCE: 100
gguguagugg uugugaaga                                                    19

<210> SEQ ID NO 101
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 30

<400> SEQUENCE: 101
uucguaccuu caguugaag                                                    19

<210> SEQ ID NO 102
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 31

<400> SEQUENCE: 102
ucguaccuuc aguugaagg                                                    19

<210> SEQ ID NO 103
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 32

<400> SEQUENCE: 103
cguaccuuca guugaagga                                                    19

<210> SEQ ID NO 104
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 33

<400> SEQUENCE: 104
caguugaagg agucaaugc                                                    19

<210> SEQ ID NO 105
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 34

<400> SEQUENCE: 105
gaaggaguca augcaccag                                                    19
```

```
<210> SEQ ID NO 106
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 35

<400> SEQUENCE: 106
cgucucguua ccuucguaa                                                  19

<210> SEQ ID NO 107
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 36

<400> SEQUENCE: 107
accuucguaa caacagcag                                                  19

<210> SEQ ID NO 108
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 37

<400> SEQUENCE: 108
cguaacaaca gcagaggag                                                  19

<210> SEQ ID NO 109
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 38

<400> SEQUENCE: 109
ucaccgaaua gguuaccaa                                                  19

<210> SEQ ID NO 110
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 39

<400> SEQUENCE: 110
caccgaauag guuaccaac                                                  19

<210> SEQ ID NO 111
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 40

<400> SEQUENCE: 111
accaacgacg gauaagacg                                                  19
```

```
<210> SEQ ID NO 112
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 41

<400> SEQUENCE: 112
cguucaaacg aaaccuacc                                               19

<210> SEQ ID NO 113
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 42

<400> SEQUENCE: 113
caaacgaaac cuacccaag                                               19

<210> SEQ ID NO 114
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 43

<400> SEQUENCE: 114
uccuuauaag ucacagguc                                               19

<210> SEQ ID NO 115
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 44

<400> SEQUENCE: 115
ccuuauaagu cacaggucc                                               19

<210> SEQ ID NO 116
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 45

<400> SEQUENCE: 116
auaagucaca ggucccagu                                               19

<210> SEQ ID NO 117
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 46

<400> SEQUENCE: 117
acauaguuag ugagagaca                                               19
```

```
<210> SEQ ID NO 118
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 47

<400> SEQUENCE: 118
agugagagac acaagaacc                                                    19

<210> SEQ ID NO 119
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 48

<400> SEQUENCE: 119
ugucgguacu uccgucaaa                                                    19

<210> SEQ ID NO 120
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 49

<400> SEQUENCE: 120
gucgguacuu ccgucaaag                                                    19

<210> SEQ ID NO 121
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 50

<400> SEQUENCE: 121
ccgucaaaga cccuaucag                                                    19

<210> SEQ ID NO 122
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 51

<400> SEQUENCE: 122
cgucgagguu uccuccuua                                                    19

<210> SEQ ID NO 123
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 52

<400> SEQUENCE: 123
uccuccuuac acgggaccu                                                    19
```

```
<210> SEQ ID NO 124
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 53

<400> SEQUENCE: 124
ccuccuuaca cgggaccuc                                                      19

<210> SEQ ID NO 125
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 54

<400> SEQUENCE: 125
acacgggacc ucuaguagu                                                      19

<210> SEQ ID NO 126
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 55

<400> SEQUENCE: 126
cuucacauaa uacugucga                                                      19

<210> SEQ ID NO 127
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 56

<400> SEQUENCE: 127
cacauaauac ugucgagug                                                      19

<210> SEQ ID NO 128
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 57

<400> SEQUENCE: 128
uagguacguc cuucuagga                                                      19

<210> SEQ ID NO 129
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 58

<400> SEQUENCE: 129
agguacgucc uucuaggac                                                      19
```

```
<210> SEQ ID NO 130
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 59

<400> SEQUENCE: 130
cuaggaccuu aaagagaug                                               19

<210> SEQ ID NO 131
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 60

<400> SEQUENCE: 131
aaagagauga guugcucga                                               19

<210> SEQ ID NO 132
<211> LENGTH: 19
<212> TYPE: RNA
<213> ORGANISM: Homo sapiens
<220> FEATURE:
<221> NAME/KEY: misc_feature
<223> OTHER INFORMATION: RNA SEQUENCE COMPLEMENTARY TO SEQ 61

<400> SEQUENCE: 132
gcucgauauu auaccuguc                                               19

<210> SEQ ID NO 133
<211> LENGTH: 19
<212> TYPE: RNA
<213> ORGANISM: Oryctolagus cuniculus

<400> SEQUENCE: 133
ccacaucacc aacgcuucu                                               19

<210> SEQ ID NO 134
<211> LENGTH: 19
<212> TYPE: RNA
<213> ORGANISM: Oryctolagus cuniculus

<400> SEQUENCE: 134
cgucaaugua ucaaucacu                                               19
```

MODULATION OF 11BETA-HYDROXYSTERIOD DEHYDROGENASE 1 EXPRESSION FOR THE TREATMENT OF OCULAR DISEASES

FIELD OF THE INVENTION

The present invention relates to methods and compositions for the treatment and/or the prevention of eye disorders related to high levels of expression or activity of 11beta-hydroxysteroid dehydrogenase 1 (11beta-HSD1); in particular but not exclusively to the treatment of glaucoma. In preferred embodiments, the invention relates to the use of RNAi technology to downregulate the expression of 11beta-HSD1.

BACKGROUND OF THE INVENTION

Glaucoma is one of the leading causes of blindness. Approximately 15% of cases of blindness world-wide result from glaucoma. The most common type, primary open-angle glaucoma, has a prevalence of 1/200 in the general population over 40 years of age. Glaucoma has been simply defined as the process of ocular tissue destruction caused by a sustained elevation of the Intra Ocular Pressure (IOP) above its normal physiological limits. Although several etiologies may be involved in the glaucoma complex, an absolute determinant in therapy selection is the amount of primary and/or induced change in pressure within the iridocorneal angle.

Current therapies include medications or surgeries aimed at lowering this pressure, although the pathophysiological mechanisms by which elevated IOP leads to neuronal damage in glaucoma are unknown. Medical suppression of an elevated IOP can be attempted using four types of drugs: (1) the aqueous humor formation suppressors (such as carbonic anhydrase inhibitors, beta-adrenergic blocking agents, and alpha2-adrenoreceptor agonists); (2) miotics (such as parasympathomimetics, including cholinergics and anticholinesterase inhibitors); (3) uveoscleral outflow enhancers; and (4) hyperosmotic agents (that produce an osmotic pressure gradient across the blood/aqueous barrier within the cilliary epithelium). A fifth category of drugs, neuroprotection agents, is emerging as an important addition to medical therapy, including, for example, NOS inhibitors, excitatory amino acid antagonists, glutamate receptor antagonists, apoptosis inhibitors, and calcium channel blockers.

Reviews of various eye disorders and their treatments can be found in the following references: Bunce et al., 2005, Associations between the deletion polymorphism of the angiotensin 1-converting enzyme gene and ocular signs of primary open-angle glaucoma. Graefes Arch Clin Exp Ophthalmol.; 243(4):294; Costagliola et al., 2000, Effect of oral losartan potassium administration on intraocular pressure in normotensive and glaucomatous human subjects. Exp Eye Res 71(2):167; Costagliola et al., 1995. Effect of oral captopril (SQ 14225) on intraocular pressure in man. Eur J Ophthalmol., 5(1):19; Cullinane et al., 2002, Renin-angiotensin system expression and secretory function in cultured human ciliary body non-pigmented epithelium. Br J Ophthalmol., 86(6):676; Sakaguchi et al., 2002, Chymase and angiotensin converting enzyme activities in a hamster model of glaucoma filtering surgery. Curr Eye Res. 24(5):325; Shah et al., 2000, Oculohypotensive effect of angiotensin-converting enzyme inhibitors in acute and chronic models of glaucoma. J Cardiovasc Pharmacol., 36(2):169, and Wang et al., 2005, Effect of CS-088, an angiotensin AT1 receptor antagonist, on intraocular pressure in glaucomatous monkey eyes. Exp Eye Res., 80(5):629.

RNA interference refers to the process of sequence-specific post-transcriptional gene silencing mediated by short interfering RNAs (siRNA). After the discovery of the phenomenon in plants in the early 1990s, Andy Fire and Craig Mello demonstrated that double-stranded RNA (dsRNA) specifically and selectively inhibited gene expression in an extremely efficient manner in *Caenorhabditis elegans* (Fire et al., 1998, Potent and specific genetic interference by double stranded RNA in *Caenorhabditis elegans*. Nature, 391:806). The sequence of the first strand (sense RNA) coincided with that of the corresponding region of the target messenger RNA (mRNA). The second strand (antisense RNA) was complementary to the mRNA. The resulting dsRNA turned out to be several orders of magnitude more efficient than the corresponding single-stranded RNA molecules (in particular, antisense RNA).

The process of RNAi begins when the enzyme, DICER, encounters dsRNA and chops it into pieces called small-interfering RNAs (siRNA). This protein belongs to the RNase III nuclease family. A complex of proteins gathers up these RNA remains and uses their code as a guide to search out and destroy any RNAs in the cell with a matching sequence, such as target mRNA (see Bosher & Labouesse, 2000, RNA interference: genetic wand and genetic watchdog. Nat Cell Biol, 2000, 2(2):E31, and Akashi et al., 2001, Suppression of gene expression by RNA interference in cultured plant cells. Antisense Nucleic Acid Drug Dev, 11(6):359).

In attempting to utilize RNAi for gene knockdown, it was recognized that mammalian cells have developed various protective mechanisms against viral infections that could impede the use of this approach Indeed, the presence of extremely low levels of viral dsRNA triggers an interferon response, resulting in a global non-specific suppression of translation, which in turn triggers apoptosis (Williams, 1997, Role of the double-stranded RNA-activated protein kinase (PKR) in cell regulation. Biochem Soc Trans, 25(2):509; Gil & Esteban, 2000, Induction of apoptosis by the dsRNA-dependent protein kinase (PKR): mechanism of action. Apoptosis, 5(2): 107-14).

In 2000 dsRNA was reported to specifically inhibit 3 genes in the mouse oocyte and early embryo. Translational arrest, and thus a PKR response, was not observed as the embryos continued to develop (Wianny & Zernicka-Goetz, 2000, Specific interference with gene function by double-stranded RNA in early mouse development. Nat Cell Bioi, 2(2):70). Research at Ribopharma AG (Kulmbach, Germany) demonstrated the functionality of RNAi in mammalian cells, using short (20-24 base pairs) dsRNA to switch off genes in human cells without initiating the acute-phase response. Similar experiments carried out by other research groups confirmed these results. (Elbashir et al., 2001, RNA interference is mediated by 21- and 22-nucleotide RNAs. Genes Dev, 15(2):188; Caplen et al., 2001, Specific inhibition of gene expression by small double stranded RNAs in invertebrate and vertebrate systems. Proc. Natl. Acad. Sci. USA, 98: 9742). Tested in a variety of normal and cancer human and mouse cell lines, it was determined that short hairpin RNAs (shRNA) can silence genes as efficiently as their siRNA counterparts (Paddison et al, 2002, Short hairpin RNAs (shRNAs) induce sequence-specific silencing in mammalian cells. Genes Dev, 16(8): 948). Recently, another group of small RNAs (21-25 base pairs) was shown to mediate downregulation of gene expression. These RNAs, small temporally regulated RNAs (stRNA), regulate timing of gene expression during development in *Caenorhabditis elegans* (for review see Banerjee & Slack, Control of developmental timing by small temporal RNAs: a paradigm for RNA-mediated regulation of gene expression. Bioessays, 2002, 24(2):119-29 and Grosshans & Slack, 2002, Micro-RNAs: small is plentiful. J Cell Biol, 156(1):17).

Scientists have used RNAi in several systems, including *Caenorhabditis elegans, Drosophila*, trypanosomes, and other invertebrates. Several groups have recently presented the specific suppression of protein biosynthesis in different mammalian cell lines (specifically in HeLa cells) demonstrating that RNAi is a broadly applicable method for gene silencing in vitro. Based on these results, RNAi has rapidly become a well recognized tool for validating (identifying and assigning) gene function. RNAi employing short dsRNA oligonucleotides will yield an understanding of the function of genes that are only partially sequenced.

As already stated, IOP is maintained by a balance between aqueous humour (AH) production (dependent on sodium transport across a ciliary epithelial bi-layer) and drainage (predominantly through the trabecular meshwork). AH is secreted into the posterior chamber of the eye flowing from the ciliary epithelium, between the iris and the lens, through the pupillary aperture, entering the anterior chamber, and finally flowing radially to the periphery, where it exits predominantly via the canal of Schlemm in the trabecular meshwork (TM), and to a lesser extent through uveoscleral outflow routes (Davson H. The aqueous humour and intraocular pressure. In: Davson's Physiology of the Eye, 5th edn. London, Macmillan Press, 1990: 3-95; Hart W M. Intraocular pressure. In: Hart W M, ed. Adler's Physiology of the Eye. St Louis, Mosby-Year Book Inc, 1992: 248-267).

In peripheral epithelial tissues, sodium and water transport are regulated by corticosteroids and the 11beta-hydroxysteroid dehydrogenase (11beta-HSD) isozymes (11beta-hydroxysteroid dehydrogenase 1 (11beta-HSD1), activating cortisol from cortisone, and 11beta-hydroxysteroid dehydrogenase 2 (11beta-HSD2), inactivating cortisol to cortisone). 11beta-HSD1 is widely expressed, most notably in many glucocorticoid target tissues including liver, adipose tissue, bone, as well as lung, vasculature, ovary and the central nervous system.

11beta-HSD expression has been described in the human eye. 11beta-HSD2 is expressed in the corneal endothelium, whereas 11beta-HSD1 is more widely expressed in the trabecular meshwork, lens epithelium and corneal epithelium (Tomlinson J W. 11 Beta-hydroxysteroid dehydrogenase type 1 in human disease: a novel therapeutic target. Minerva Endocrinol. 2005 March; 30(1):37-46).

11beta-HSD1 but not 11beta-HSD2 has been localized in the human non-pigmented neuroepithelial cells or NPE (Rauz S, Walker E A, Shackleton C H L, Hewison M, Murray P I, Stewart P M. Expression and putative role of 11β-hydroxysteroid dehydrogenase isozymes within the human eye. Invest Ophthalmol Vis Sci 2001; 42:2037-42; Suzuki T, Sasano H, Kaneko C, Ogawa S, Darnel A D, Krozowski Z S. Immunohistochemical distribution of 11β-hydroxysteroid dehydrogenase in human eye. Mol Cell Endocrinol 2001; 173:121-5; Mirshahi M, Nicolas C, Mirshahi A, Hecquet C, d'Hermies F, Faure J P, et al. The mineralocorticoid hormone receptor and action in the eye. Biochem Biophys Res Commun 1996; 219:150-6; Stokes J, Noble J, Brett L, Philips C, Seckl J R, O'Brien C, et al. Distribution of glucocorticoid and mineralocorticoid receptors and 11β-hydroxysteroid dehydrogenases in human and rat ocular tissues. Invest Ophthalmol Vis Sci 2000; 41:1629-38). In situ hybridization defined expression of 11beta-HSD1 in the ciliary epithelium, while RT-PCR analysis of ciliary body tissue confirmed expression of 11beta-HSD1, with additional glucocorticoid receptor and mineralocorticoid receptor (Rauz S, Cheung C M, Wood P J, Coca-Prados M, Walker E A, Murray P I, Stewart P M. Inhibition of 11beta-hydroxysteroid dehydrogenase type 1 lowers intraocular pressure in patients with ocular hypertension. QJM., 2003 July; 96(7):481-90). The enzyme 11beta-HSD1 plays a pivotal role in determining intracellular glucocorticoid concentrations by regenerating, in a reversible reaction, active glucocorticoid (cortisol in humans, corticosterone in rats and mice) from inactive cortisone and 11-dehydrocorticosterone. A high cortisol/cortisone ratio of 14:1 has been documented in aqueous humour, consistent with this local cortisol-generating system (Rauz S, Walker E A, Shackleton C H L, Hewison M, Murray P I, Stewart P M. Expression and putative role of 11β-hydroxysteroid dehydrogenase isozymes within the human eye. Invest Ophthalmol Vis Sci 2001; 42:2037-42).

Oral administration of carbenoxolone (CBX), an inhibitor of 11beta-HSD1, to volunteers in a pilot uncontrolled study, resulted in a decrease of IOP of 17.5%, suggesting that 11beta-HSD1 activity may partly regulate sodium transport across the NPE-pigmented bi-layer, and consequently aqueous humour secretion (Rauz S, Walker E A, Shackleton C H L, Hewison M, Murray P I, Stewart P M. Expression and putative role of 11β-hydroxysteroid dehydrogenase isozymes within the human eye. Invest Ophthalmol Vis Sci 2001; 42:2037-42). Further, randomised, placebo-controlled studies of healthy volunteers and patients with ocular hypertension (raised IOP but no optic neuropathy) assessed the effect of CBX on IOP (Rauz S, Cheung C M, Wood P J, Coca-Prados M, Walker E A, Murray P I, Stewart P M. Inhibition of 11beta-hydroxysteroid dehydrogenase type 1 lowers intraocular pressure in patients with ocular hypertension. QJM., 2003 July; 96(7):481-90).

The preceding is a discussion of relevant art pertaining to RNAi. The discussion is provided only for understanding of the invention that follows, and is not an admission that any of the work described is prior art to the claimed invention.

SUMMARY OF THE INVENTION

In the present invention we provide methods and compositions for modulating the expression and/or activity of 11beta-hydroxysteroid dehydrogenase 1 (11beta-HSD1) by means of the use of siNA for the treatment of eye conditions. In preferred embodiments the eye conditions are characterised by an altered IOP in animals, including humans. In particular, the eye condition is glaucoma.

Another aspect of the present invention relates to an isolated siNA compound comprising a sequence complementary to a nucleotide sequence selected from SEQ ID NO 1 to SEQ ID NO 61 or comprising a nucleotide sequences selected from the group SEQ ID NO 62 to SEQ ID NO 122.

Yet another aspect of the present invention relates to pharmaceutical compositions comprising siNA compounds targeted to 11beta-HSD1.

In addition to the treatment of glaucoma, the present method is also suitable for the treatment of other diseases of the anterior chamber of the eye. In particular, the method may be applied to the treatment of diseases characterised by altered aqueous formation or outflow in the eye. Examples of conditions which may be treated according to the invention include local conditions such as infections or inflammations, and general conditions such as uveitis or expression of systemic diseases. Further, certain embodiments of the invention provide treatment for diabetic retinopathy.

Downregulation may be effected by the use of double stranded nucleic acid moieties, named siNA or small interfering NA that are directed at interfering with the mRNA expression of 11beta-HSD1. The siNA are preferably siRNA, although modified nucleic acids or similar chemically synthesised entities are also included within the scope of the invention.

Preferred embodiments of the invention relate to topical application of siNA. Embodiments of the invention also provide pharmaceutical compositions for use in the treatment of eye conditions. The invention may be used within the fields of local eye treatments, of target genes involved in glaucoma pathogenesis, as well as the use of chemically synthesized entities to treat animals (including humans).

DESCRIPTION OF THE DRAWINGS

FIG. 1 shows GenBank Accession Numbers corresponding to the two alternative transcripts of 11beta-HSD.

FIGS. 2A-C show short fragments of the target gene sequence chosen as the target sequences of the siNA of the invention.

FIGS. 3A-D show siNA molecules of the invention.

Figure 4:
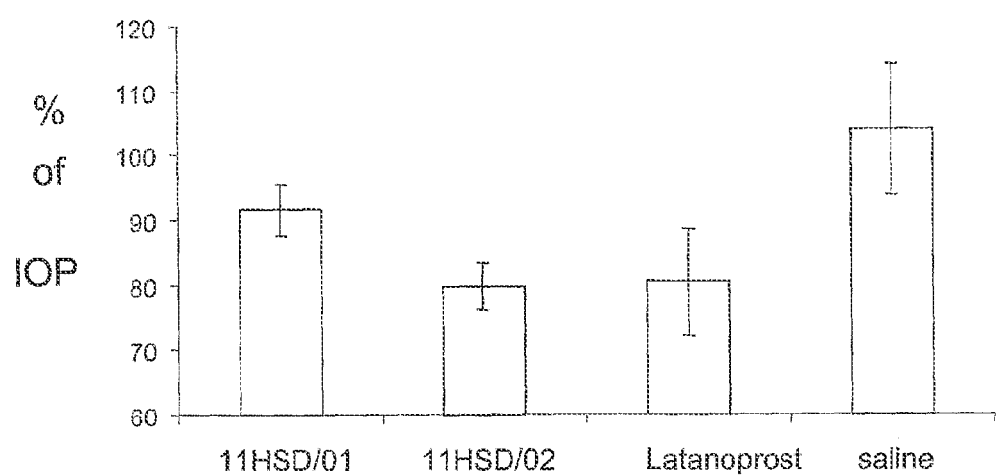
FIG. 4 shows maximum effect of two siRNAs on the reduction of IOP in normotensive New Zealand rabbits. The values represent the mean of the percentage of IOP reduction over the control (contralateral eye with vehicle alone) and their standard error (SD). The siRNAs used are 11HSD/01: CCACAUCACCAACGCUUCUdTdT (SEQ ID 133; rabbit sequence homologous to human SEQ ID No 100) and 11HSD/02: CGUCAAUGUAUCAAUCACUdTdT (SEQ ID 134; rabbit sequence with best score and with no corresponding disclosed human sequence).

Each value represents the mean of the percentage of IOP reduction over the control (contralateral eye with vehicle alone) in four different animals.

DETAILED DESCRIPTION OF THE INVENTION

In a first aspect, the invention relates to the use of siNA in the manufacture of a medicament for the treatment of an eye condition, wherein said siNA is capable of inhibiting expression of 11beta-hydroxysteroid dehydrogenase 1 (11beta-HSD1).

The term inhibiting as used according to the invention encompasses downregulation of 11beta-HSD1. In one embodiment, the eye condition according to the invention is characterised by an altered intra-ocular pressure (IOP) in the patient. In another embodiment, the eye condition is selected from the group comprising glaucoma, infection, inflammation, uveitis, and expression of systemic diseases. The eye condition may be selected from glaucoma or diabetic retinopathy. According to the invention, target gene expression may be inhibited in the eye of the patient.

In one embodiment, the siNA according to the invention is siRNA. Preferably, the siRNA is dsRNA.

Although the mechanisms for RNAi remain unknown, the steps required to generate the specific dsRNA oligonucleotides are clear. It has been shown that dsRNA duplex strands that are 21-26 nucleotides in length work most effectively in producing RNA interference. Accordingly, in one embodiment, the siNA of the invention is of 21-26 nucleotides in length. However, the length of the siNA compound according to the invention is not limited. Selecting the right homologous region within the gene is also important. Factors such as the distance from start codon, the G/C content and the location of adenosine dimers are important when considering the generation of dsRNA for RNAi. One consequence of this, however, is that one may need to test several different sequences for the most efficient RNAi and this may become costly.

In 1999, Tuschl et al. (Targeted mRNA degradation by double-stranded RNA in vitro. Genes Dev., 1999; 13(24): 3191-7) deciphered the silencing effect of siRNAs showing that their efficiency is a function of the length of the duplex, the length of the 3'-end overhangs, and the sequence in these overhangs. Based on this founder work, Eurogentec recommends that the target mRNA region, and hence the sequence of the siRNA duplex, should be chosen using the following guidelines:

Since RNAi relies on the establishment of complex protein interactions, it is obvious that the mRNA target should be devoid of unrelated bound factors. In this context, both the 5' and 3' untranslated regions (UTRs) and regions close to the start codon should be avoided as they may be richer in regulatory protein binding sites. The sequence of the siRNA is therefore selected as follows: In the mRNA sequence, a region located 50 to 100 nt downstream of the AUG start codon or upstream of stop codon is selected.

In this region, the following sequences are searched for: AA(N19), CA(N19). The G/C percentage for each identified sequence is calculated. Ideally, the G/C content is 50% but it must less than 70% and greater than 30%.

Preferably, sequences containing following repetitions are avoided: AAA, CCC, GGG, TTT, AAAA, CCCC, GGGG, TTTT.

An accessibility prediction according to the secondary structure of the mRNA is carried out as well. A BLAST is also performed (i.e. NCBI ESTs database) with the nucleotide sequence fitting best the previous criteria to ensure that only one gene will be inactivated.

In order to maximize the result's interpretation, the following precautions should be taken when using siRNAs:
  Always test the sense and antisense single strands in separate experiments.
  Try a scramble siRNA duplex. This should have the same nucleotide composition as your siRNA but lack significant sequence homology to any other gene (including yours).
  If possible, knock-down the same gene with two independent siRNA duplexes to control the specificity of the silencing process.

Practically, each of the selected genes is introduced as a nucleotide sequence in a prediction program that takes into account all the variables described above for the design of optimal oligonucleotides. This program scans any mRNA nucleotide sequence for regions susceptible to be targeted by siRNAs. The output of this analysis is a score of possible siRNA oligonucleotides. The highest scores are used to design double stranded RNA oligonucleotides (typically 21 bp long, although other lengths are also possible) that are typically made by chemical synthesis.

The nucleotides according to the invention may comprise one or more modified oligonucleotides. The one or more modifications are aimed at increasing stability or availability of the siNA. Examples of suitable modifications are described in the publications referenced below, each of which is incorporated herein by reference. Examples of such modifications according to the invention include, but are not limited to, phosphorothioate internucleotide linkages, 2'-O-methyl ribonucleotides, 2'-deoxy-fluoro ribonucleotides, 2'-deoxy ribonucleotides, "universal base" nucleotides, 5-C-methyl nucleotides, and inverted deoxyabasic residue incorporation, chemical cross linking between the two complementary strands of an siRNA and chemical modification of a 3' terminus of a strand of an siRNA, internal modifications, for example, sugar modifications, nucleobase modifications and/or backbone modifications. 2'-fluoro modified ribonucleotides and 2'-deoxy ribonucleotide.

Studies show that replacing the 3'-terminal nucleotide overhanging segments of a 21-mer siRNA duplex having two-nucleotide 3'-overhangs with deoxyribonucleotides does not have an adverse effect on RNAi activity. Replacing up to four nucleotides on each end of the siRNA with deoxyribonucleotides has been reported to be well tolerated, whereas complete substitution with deoxyribonucleotides results in no RNAi activity (Elbashir 2001). In addition, Elbashir et al. also report that substitution of siRNA with 2'-O-methyl nucleotides completely abolishes RNAi activity.

Affinity modified nucleosides as described in WO2005/044976 may be used. This publication describes oligonucleotides comprising nucleosides modified so as to have increased or decreased affinity for their complementary nucleotide in the target mRNA and/or in the complementary siNA strand.

GB2406568 describes alternative modified oligonucleotides chemically modified to provide improved resistance to degradation or improved uptake. Examples of such modifications include phosphorothioate internucleotide linkages, 2'-O-methyl ribonucleotides, 2'-deoxy-fluoro ribonucleotides, 2'-deoxy ribonucleotides, "universal base" nucleotides, 5-C-methyl nucleotides, and inverted deoxyabasic residue incorporation.

WO2004/029212 describes oligonucleotides modified to enhance the stability of the siRNA or to increase targeting efficiency. Modifications include chemical cross-linking between the two complementary strands of an siRNA and chemical modification of a 3' terminus of a strand of an siRNA. Preferred modifications are internal modifications, for example, sugar modifications, nucleobase modifications and/or backbone modifications. 2'-fluoro modified ribonucleotides and 2'-deoxy ribonucleotides are described.

WO2005/040537 further recites modified oligonucleotides which may be used in the invention.

As well as making use of dsNA and modified dsNA, the present invention may use short hairpin NA (shNA); the two strands of the siNA molecule may be connected by a linker region, which may be a nucleotide linker or a non-nucleotide linker.

In addition to siNA according to the invention which is complementary to the sequence in the mRNA target region, degenerate siNA sequences may be used to target homologous regions according to the invention. Degenerate siNA sequences can be designed according to methods known to the skilled person. For example, WO2005/045037 describes the design of siNA molecules to target such homologous sequences, for example by incorporating non-canonical base pairs, for example mismatches and/or wobble base pairs, that can provide additional target sequences. In instances where mismatches are identified, non-canonical base pairs (for example, mismatches and/or wobble bases) can be used to generate siNA molecules that target more than one gene sequence. In a non-limiting example, non-canonical base pairs such as UU and CC base pairs are used to generate siNA molecules that are capable of targeting sequences for differing targets that share sequence homology. As such, one advantage of using siNAs of the invention is that a single siNA can be designed to include nucleic acid sequence that is complementary to the nucleotide sequence that is conserved between homologous genes. In this approach, a single siNA can be used to inhibit expression of more than one gene instead of using more than one siNA molecule to target different genes.

Preferred siNA molecules of the invention are double stranded. A siNA molecule of the invention may comprise blunt ends, that is, ends that do not include any overhanging nucleotides. In one embodiment, a siNA molecule of the invention can comprise one or more blunt ends. In preferred embodiments, the siNA molecules have 3' overhangs. siNA molecules of the invention may comprise duplex nucleic acid molecules with 3' overhangs of n nucleotides (5≧n≧1). Elbashir (2001) shows that 21-nucleotide siRNA duplexes are most active when containing 3'-terminal dinucleotide overhangs.

Candidate oligonucleotides are further filtered for interspecies sequence conservation in order to facilitate the transition from animal to human clinical studies. In preferred embodiments of the invention, conserved oligonucleotides are used; this allows a single oligonucleotide sequence to be used in both animal models and human clinical trials.

The present invention may comprise the administration of one or more species of siNA molecule simultaneously. These one or more species may be selected to target the same or different mRNA species. Preferably, the siNA is targeted to a sequence selected from SEQ ID 1 to SEQ ID 61 or to a sequence comprising SEQ ID 1 to SEQ ID 61.

GenBank Accession Numbers corresponding to the two alternative transcripts of 11 beta-HSD are displayed in FIG. 1. The present invention allows individual targeting of each transcript form. Thus, in one embodiment, the siNA is targeted to a splice form of 11 beta-HSD as displayed in FIG. 1.

Selected oligonucleotide sequences against which RNAi is directed are shown in FIG. 2. Displayed sequences are the DNA sequences targeted by the siNA. Therefore, the invention makes use of NA duplexes with sequences complementary to the indicated DNA sequences.

The sequences shown in FIG. 2 are not limiting. Target DNA need not necessarily be preceded by AA or CA. Further, target DNA could be constituted by sequences included in FIG. 2 flanked by any contiguous sequence.

In another aspect, the invention relates to a method of treatment of an eye condition, comprising administering siNA wherein said siNA is capable of inhibiting expression of 11beta-HSD1. The siNA is defined according to the invention.

In a further aspect, the invention also relates to a method of inhibiting the expression of 11beta-HSD1 comprising administering a siNA compound capable of inhibiting expression of 11beta-HSD1. The siNA is defined according to the invention.

In another aspect, the invention relates to an isolated siNA compound targeted to 11beta-HSD1 wherein the siNA compound comprises a sequence complementary to a nucleotide sequence selected from SEQ ID 1 to SEQ ID 61. The siNA compound may in one embodiment comprise a nucleotide sequences selected from the group SEQ ID NO 62 to SEQ ID NO 122. In particular, the invention relates to an isolated siNA molecule comprising a sequence complementary to a nucleotide sequence selected from SEQ ID 1 to SEQ ID 61 or SEQ ID No 62 to 122 for use as a medicament.

In a final aspect, the invention relates to a pharmaceutical composition comprising an isolated siNA compound as described herein. In one embodiment, the pharmaceutical composition comprises an isolated siNA compound targeted to 11beta-HSD1 wherein the siNA compound comprises a sequence complementary to a nucleotide sequence selected from SEQ ID 1 to SEQ ID 61 or comprising a nucleotide sequences selected from the group SEQ ID NO 62 to SEQ ID NO 122.

The siNA molecules of the invention and formulations or compositions thereof may be administered directly or topically (e.g., locally) to the eye as is generally known in the art. For example, a siNA molecule can comprise a delivery vehicle, including liposomes, for administration to a subject. Carriers and diluents and their salts can be present in pharmaceutically acceptable formulations. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins poly (lactic-co-glycolic) acid (PLGA) and PLCA microspheres, biodegradable nanocapsules, and bioadhesive microspheres, or by proteinaceous vectors. In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

A siNA molecule of the invention may be complexed with membrane disruptive agents and/or a cationic lipid or helper lipid molecule.

Delivery systems which may be used with the invention include, for example, aqueous and non aqueous gels, creams, multiple emulsions, microemulsions, liposomes, ointments, aqueous and non aqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

A pharmaceutical formulation of the invention is in a form suitable for administration, e.g., systemic or local administration, into a cell or subject, including for example a human. Suitable forms, in part, depend upon the use or the route of entry, for example oral, transdermal, or by injection. Other factors are known in the art, and include considerations such as toxicity and forms that prevent the composition or formulation from exerting its effect.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art. For example, preservatives, stabilizers, dyes and flavouring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize.

Generally, an amount between 0.1 mg/kg and 100 mg/kg body weight/day of active ingredients is administered.

The formulations of the invention can be administered in dosage unit formulations containing conventional non-toxic pharmaceutically acceptable carriers, adjuvants and/or vehicles. Formulations can be in a form suitable for oral use, for example, as tablets, troches, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions can contain one or more such sweetening agents, flavouring agents, colouring agents or preservative agents in order to provide pharmaceutically elegant and palatable preparations. Tablets contain the active ingredient in admixture with non-toxic pharmaceutically acceptable excipients that are suitable for the manufacture of tablets.

These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more colouring agents, one or more flavouring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavouring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavouring and colouring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavouring agents.

Syrups and elixirs can be formulated with sweetening agents, for example glycerol, propylene glycol, sorbitol, glucose or sucrose. Such formulations can also contain a demulcent, a preservative and flavouring and colouring agents. The pharmaceutical compositions can be in the form of a sterile injectable aqueous or oleaginous suspension.

This suspension can be formulated according to the known art using those suitable dispersing or wetting agents and suspending agents that have been mentioned above.

A sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The nucleic acid molecules of the invention can also be administered in the form of suppositories, e.g. for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

Alternatively, certain siNA molecules of the invention can be expressed within cells from eukaryotic promoters. Recombinant vectors capable of expressing the siNA molecules can be delivered and persist in target cells. Alternatively, vectors can be used that provide for transient expression of nucleic acid molecules. Such vectors can be repeatedly administered as necessary. Once expressed, the siNA molecule interacts with the target mRNA and generates an RNAi response. Delivery of siNA molecule expressing vectors can be systemic, such as by intravenous or intra-muscular administration, by administration to target cells ex-planted from a subject followed by reintroduction into the subject, or by any other means that would allow for introduction into the desired target cell.

EXAMPLES

Obtaining siRNA Duplexes

RNAs are preferably chemically synthesized using appropriately protected ribonucleoside phosphoramidites and a conventional DNA/RNA synthesizer. Substitution of one or both strands of a siRNA duplex by 2'-deoxy or 2'-O-methyl oligoribonucleotides abolishes silencing in fly extract (Elbashir et al. 2001). In mammalian cells, however, it seems possible to substitute the sense siRNA by a 2'-O-methyl oligoribonucleotide (Ge et al. RNA interference of influenza virus production by directly targeting mRNA for degradation and indirectly inhibiting all viral RNA transcription. Proc Natl Acad Sci USA., 2003; 100(5):2718-23).

Most conveniently, siRNAs are obtained from commercial RNA oligo synthesis suppliers, which sell RNA-synthesis products of different quality and costs. In general, 21-nt RNAs are not too difficult to synthesize and are readily provided in a quality suitable for RNAi.

Suppliers of RNA synthesis reagents include Proligo (Hamburg, Germany), Dharmacon Research (Lafayette, Colo., USA), Glen Research (Sterling, Va., USA), ChemGenes (Ashland, Mass., USA), and Cruachem (Glasgow, UK), Qiagen (Germany), Ambion (USA) and Invitrogen (Scotland). The previous custom RNA synthesis companies are entitled to provide siRNAs with a license for target validation. In particular, our siRNA suppliers are Ambion, Dharmacon and Invitrogen, companies that offer the traditional custom chemical synthesis service for siRNA, and supply the siRNA with HPLC purification and delivered in dry form along with RNase-free water. A central web-based resource for RNAi and siRNA methodologies, along with links to additional siRNA related products and services, can be found on the website of above-mentioned suppliers.

An annealing step is necessary when working with single-stranded RNA molecules. It is critical that all handling steps be conducted under sterile, Rnase free conditions. To anneal the RNAs, the oligos must first be quantified by UV absorption at 260 nanometers (nm). The following protocol based on Elbashir et al. (2001) is then used for annealing:

Separately aliquot and dilute each RNA oligo to a concentration of 50 µM.

Combine 30 µl of each RNA oligo solution and 15 µl of 5× annealing buffer. Final buffer concentration is: 100 mM potassium acetate, 30 mM HEPES-KOH pH 7.4, 2 mM magnesium acetate. Final volume is 75 µl.

Incubate the solution for 1 minute at 90° C., centrifuge the tube for 15 seconds, let sit for 1 hour at 37° C., then use at ambient temperature. The solution can be stored frozen at −20° C. and freeze-thawed up to 5 times. The final concentration of siRNA duplex is usually 20 µM.

Alternatively, already annealed dsRNAs may be purchased from the suppliers.

Chemically modified nucleic acids may also be used. For example, an overview of the types of modification which may be used is given in WO03/070744, the contents of which are incorporated herein by reference. Particular attention is drawn to pages 11 to 21 of this publication. Other possible modifications are as described above. The skilled person will be aware of other types of chemical modification which may be incorporated into RNA molecules.

"In Vitro" System

To check the specificity of the siRNA interference, different cell cultures that express the target genes such as non-pigmented ciliary epithelium cells NPE, ciliary epithelium cells OMDC, or embryonic kidney cells HEK293, are employed. Alternatively, cell bladder carcinoma cell line T-24, lung carcinoma cell line A549 or human embryonic keratinocytes HEK are used.

The cells are incubated with the corresponding siRNA duplexes, and analysis of the downregulation of expression of the target gene is carried out. For linking siRNA knockdown to specific phenotypes in cultured cells, it is necessary to demonstrate the reduction of targeted protein or at least demonstrate the reduction of the targeted mRNA.

mRNA levels of the target gene are quantitated by real-time quantitative PCR (RT-PCR). Further, the protein levels can be determined in a variety of ways well known in the art, such as Western blot analysis with specific antibodies to the different target allow direct monitoring of the reduction of targeted protein.

Transfection of siRNA Duplexes

Several examples of techniques well known in the art are as follows: We can perform a single transfection of siRNA duplex using a cationic lipid, such as RNAiFect Transfection Reagent (Qiagen) and Lipofectamine 2000 Reagent (Invitrogen) and assay for silencing 24, 48 and 72 hours after transfection.

A typical transfection protocol can be performed as follows: For one well of a 6-well plate, we transfect using 100 nM as final concentration of siRNA. Following RNAiFect protocol, we seed, the day before transfection, 2-4×10$^5$ cells per well in 3 ml of an appropriate growth medium, containing DMEM, 10% serum, antibiotics and glutamine, and incubate cells under normal growth conditions (37° C. and 5% $CO_2$). On the day of transfection, cells have to be at 30-50% confluence. We dilute 15 ul of 20 uM siRNA duplex (corresponding to 100 nM final concentration) in 85 ul of Buffer EC-R, to give a final volume of 100 ul and mix by vortexing. For complex formation, we add 19 ul of RNAiFect Transfection Reagent to the diluted siRNA and mix by pipetting or vortexing. After incubating the samples for 10-15 minutes at room temperature to allow formation of transfection complexes, we add the complexes drop-wise onto the cells with 2.9 ml of fresh growth medium low in antibiotics. After swirling the plates to ensure uniform distribution of the transfection complexes, we incubate the cells under their normal growth conditions. The day after, the complexes are removed and fresh and complete growth medium is added. To monitor gene silencing, cells are collected at 24, 48 and 72 hours post-transfection. The Lipofectamine 2000 Reagent protocol is quite similar. The day before transfection, we seed 2-4×10$^5$ cells per well in 3 ml of an appropriate growth medium, containing DMEM, 10% serum, antibiotics and glutamine, and incubate cells under normal growth conditions (37° C. and 5% $CO_2$). On the day of transfection, cells have to be at 30-50% confluence. We dilute 12.5 ul of 20 uM siRNA duplex (corresponding to 100 nM final concentration) in 250 ul of DMEM, to give a final volume of 262.5 ul, and mix. Also, 6 ul of Lipofectamine 2000 is diluted in 250 ul of DMEM and mixed. After a 5 minutes incubation at room temperature, the diluted oligomer and the diluted Lipofectamine are combined to allow complex formation during a 20 minutes incubation at room temperature. Afterwards, we add the complexes drop-wise onto the cells with 2 ml of fresh growth medium low in antibiotics and mix gently by rocking the plate back and forth, to ensure uniform distribution of the transfection complexes. We incubate the cells under their normal growth conditions and the day after, the complexes are removed and fresh and complete growth medium is added. To monitor gene silencing, cells are collected at 24, 48 and 72 hours post-transfection.

The efficiency of transfection may depend on the cell type, but also on the passage number and the confluency of the cells. The time and the manner of formation of siRNA-liposome complexes (e.g. inversion versus vortexing) are also critical. Low transfection efficiencies are the most frequent cause of unsuccessful silencing. Good transfection is a non-trivial issue and needs to be carefully examined for each new cell line to be used. Transfection efficiency may be tested transfecting reporter genes, for example a CMV-driven EGFP-expression plasmid (e.g. from Clontech) or a B-Gal expression plasmid, and then assessed by phase contrast and/or fluorescence microscopy the next day.

Testing of siRNA Duplexes

Depending on the abundance and the life time (or turnover) of the targeted protein, a knock-down phenotype may become apparent after 1 to 3 days, or even later. In cases where no phenotype is observed, depletion of the protein may be observed by immunofluorescence or Western blotting.

After transfections, total RNA fractions extracted from cells are pre-treated with DNase I and used for reverse transcribed using a random primer. PCR is amplified with a specific primer pair covering at least one exon-exon junction in order to control for amplification of pre-mRNAs. RT/PCR of a non-targeted mRNA is also needed as control. Effective depletion of the mRNA yet undetectable reduction of target protein may indicate that a large reservoir of stable protein may exist in the cell. Alternatively, RealTime PCR amplification can be used to test in a more precise way the mRNA decrease or disappearance. Real-time reverse-transcriptase (RT) PCR quantitates the initial amount of the template most specifically, sensitively and reproducibly. Real-time PCR monitors the fluorescence emitted during the reaction as an indicator of amplicon production during each PCR cycle. This signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template.

To verify the interference pattern of the differentially expressing genes identified in the cell cultures, qRT-PCR is performed according to the manufacturer protocol. For quantitative RT-PCR (qRT-PCR), approximately 250 ng of total RNA is used for reverse transcription followed by PCR amplification with specific primers for each gene in reaction mixture containing Master SYBR Green I. Basic PCR conditions comprised an initial step of 30 minutes at 91° C., followed by 40 cycles of 5 s at 95° C., 10 s at 62° C. and 15 s at 72° C. Specific primer sequences corresponding to each target gene are used. Quantification of b-actin mRNA is used as a control for data normalization. Relative gene expression comparisons work best when the gene expression of the chosen endogenous/internal control is more abundant and remains constant, in proportion to total RNA, among the samples. By using an invariant endogenous control as an active reference, quantitation of an mRNA target can be normalised for differences in the amount of total RNA added to each reaction.

Animal Studies

The New Zealand rabbit is the gold standard in experimental platform designed to study IOP. It is easy to handle and it has a big eye, similar in size to the human organ. In addition, present equipment to measure IOP is not suited to use in animals with small eyes such as mice or rats. Finally, rabbits have an IOP (around 23 mm Hg) that can be brought down to up to 40% its value using local commercial hypotensive medication. Thus, although it is possible to generate rabbit glaucoma models (for example, surgically blocking episcleratic veins or artificially occluding the trabecular meshwork), we have used normotensive rabbits since, in our hands, the pharmacological decrease in IOP can be easily and reproducibly measured.

Experimental Protocol

Normotensive New Zealand White rabbits (males, 2-3 kg) were used. The animals were kept in individual cages with free access to food and water. They were submitted to artificial 12 hours light/darkness cycles, to avoid uncontrolled circadian oscillations of IOP Animal handling and treatment were carried out in accordance with the European Communities Council Directive (86/609/EEC) and the statement of the Association for Research in Vision and Ophthalmology on the Use of Animals in Ophthalmic and Vision Research.

The drugs were typically administered by instilling a small volume (typically 40 µL) on the corneal surface. Contralateral eyes were treated with the vehicle alone and could be used as controls in each experiment lest there is a sympathy phenomenon with the other eye. Multiple experiments in the same animal should be abolished.

IOP measurements were done using a contact tonometer (TONOPEN XL, Mentor, Norwell, Mass.). The TonoPen tonometer is very convenient due to its reliability and small size. Measurements with this instrument were performed delicately applying the tonometer's sensor to the corneal surface. This device has been shown to be the tonometer of choice for measuring intraocular pressures within the range of 3 to 30 mm Hg in rabbits (Abrams et al. Comparison of three tonometers for measuring intraocular pressure in rabbits. Invest Ophthalmol Vis Sci. 1996 April; 37(5):940-4.). All measurements fell within this interval: the mean baseline value of intraocular pressure was 17.0±0.39 mm Hg (n=100). Because IOP changes from the night to day, all the experiments were performed at the same time to allow IOP more stable and permit an objective comparison with vehicle treatment. In order to avoid distress to the animal, rabbits were topically anesthetized (oxibuprocaine/tetracaine, 0.4%/1%, in a saline solution (1/4 v:v). The solution was applied (10 µl) to the cornea before each measurement of intraocular pressure was made. siRNA or saline was applied topically to the cornea in volumes of 40 µl.

The standard protocol for the siRNA application in rabbit was as follows. Doses of siRNA in saline solution (0.9% w/v) to a final volume of 40 ul, were applied to one eye each day during four consecutive days. The opposite eye was taken as a control and 40 µl of sterile saline (0.9% w/v) were instilled on it, at the same time points. The IOP was measured before each application and at 2 h, 4 h and 6 h following the instillation, during 10 days. Maximum responses were observed between second and third day. To compare the effect of siRNA with other hypotensive compounds, Xalatan (latanoprost 0.005%) and Trustop (Dorzolamide 2%) were assayed and IOP measured in the same conditions.

Rabbits were treated based on the standard protocol described above. These experiments demonstrated the maximum effect of two siRNAs on the reduction of IOP in normotensive New Zealand rabbits. The values in FIG. 4 represent the mean of the percentage of IOP reduction over the control (contralateral eye with vehicle alone) and their standard error (SD). The siRNAs used are 11HSD/01: CCACAUCACCAACGCUUCUdTdT (SEQ ID 133; rabbit sequence homologous to human SEQ ID No 100) and 11HSD/02: CGUCAAUGUAUCAAUCACUdTdT (SEQ ID 134; rabbit sequence with best score and with no corresponding disclosed human sequence).

Figure 5:
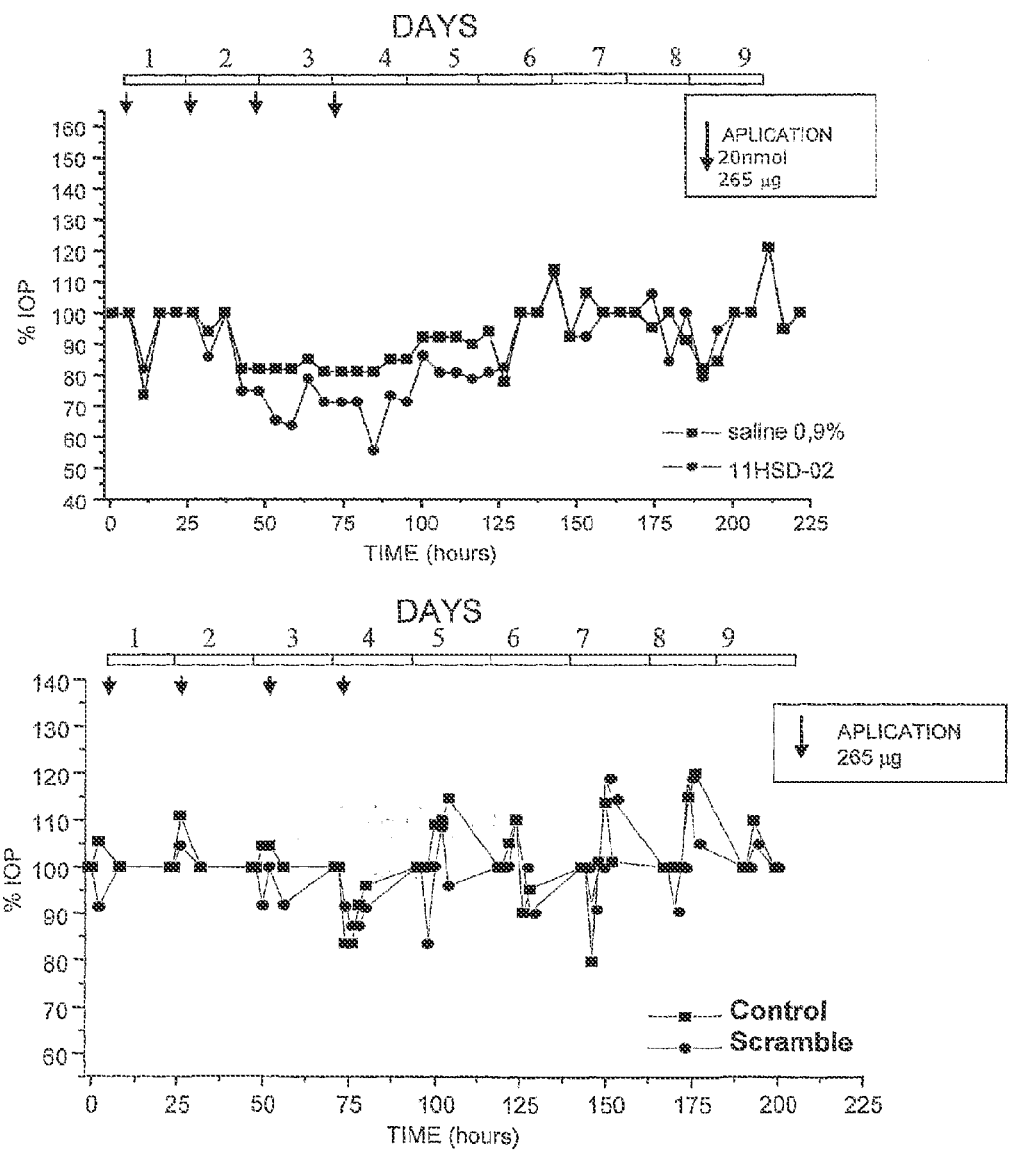
FIG. 5 shows in vivo effect of siRNA 11HSD/02 on the reduction of IOP in normotensive New Zealand rabbit across de time. Four consecutive applications of 265 ug of siRNA produced a decrease on IOP of 20.34 over control. In contrast, a scramble siRNA had not any effect on IOP levels.

The results also show in vivo effect of siRNA 11HSD/02 on the reduction of IOP in normotensive New Zealand rabbit across de time (FIG. 5). Four consecutive applications of 265 ug of siRNA produced a decrease on IOP of 20.34 over control. In contrast, a scramble siRNA had not any effect on IOP levels. Each value represents the mean of the percentage of IOP reduction over the control (contralateral eye with vehicle alone) in four different animals.

The invention claimed is:

1. A method of treating an eye condition characterized by increased intra-ocular pressure (IOP), said method comprising topically administering to the corneal surface of the eye of a patient in need thereof a short interfering nucleic acid (siNA) molecule that downregulates expression of 11betahydroxysteroid dehydrogenase 1 (11beta-HSD1) in the eye.

2. The method according to claim 1, wherein the eye condition is selected from the group consisting of glaucoma, infection, inflammation, uveitis, and expression of systemic diseases.

3. The method according to claim 1, wherein the eye condition is glaucoma.

4. The method according to claim 1, wherein the eye condition is diabetic retinopathy.

5. The method according to claim 1, wherein the siNA is siRNA.

6. The method according to claim 5, wherein the siRNA is dsRNA.

7. The method according to claim 5, wherein the siRNA is shRNA.

8. The method according to claim 1, wherein the siNA comprises one or more modified oligonucleotides.

9. The method according to claim 1, wherein a plurality of species of siNA are used.

10. The method according to claim 1, wherein the siNA is targeted to a sequence selected from SEQ ID NO 1 to SEQ ID NO 61, or to a sequence comprising SEQ ID NO 1 to SEQ ID NO 61.

11. The method according to claim 1, wherein the siNA molecules of the invention comprise nucleotide sequences selected from SEQ ID NO 62 to SEQ ID NO 122.

12. The method according to claim 11 wherein the siNA molecules contain dinucleotide 3' overhangs.

13. The method of claim 1, wherein said topically administering consists of instilling said siNA molecule on said corneal surface.

* * * * *